United States Patent
Schiefer

(10) Patent No.: US 8,921,766 B2
(45) Date of Patent: Dec. 30, 2014

(54) ROTATIONALLY SYMMETRICAL COHERENT VERIFICATION PHANTOM (VIRTUAL PATIENT) WITH A FLAT DETECTOR DISPOSED ON A ROTARY AXIS INTEGRATED IN A MULTI PURPOSE QC-ACCESSORY

(75) Inventor: Hans Schiefer, Eggersriet (CH)

(73) Assignee: John Brent Moetteli

( * ) Notice: Subject to any disclaimer, the term of this patent is extended or adjusted under 35 U.S.C. 154(b) by 102 days.

(21) Appl. No.: 13/577,665

(22) PCT Filed: Feb. 9, 2011

(86) PCT No.: PCT/IB2011/000224
§ 371 (c)(1),
(2), (4) Date: Aug. 8, 2012

(87) PCT Pub. No.: WO2011/098891
PCT Pub. Date: Aug. 18, 2011

(65) Prior Publication Data
US 2012/0305793 A1      Dec. 6, 2012

Related U.S. Application Data

(60) Provisional application No. 61/302,550, filed on Feb. 9, 2010, provisional application No. 61/412,407, filed on Nov. 11, 2010, provisional application No. 61/418,439, filed on Dec. 1, 2010.

(51) Int. Cl.
*H04N 5/33* (2006.01)
*A61B 18/20* (2006.01)
*A61N 5/10* (2006.01)

(52) U.S. Cl.
CPC .................... *A61N 5/1048* (2013.01)
USPC .......................... 250/252.1; 606/11

(58) Field of Classification Search
CPC .................... A61N 5/1048; A61N 5/1071
USPC .......................... 250/252.1; 606/11
See application file for complete search history.

(56) References Cited

U.S. PATENT DOCUMENTS 7,471,765 B2 * 12/2008 Jaffray et al. .............. 378/65
2003/0004503 A1   1/2003 Nilsson et al.

OTHER PUBLICATIONS

Bedford et al., Note; Evaluation of the Delta4 phantom for IMRT and VMAT verification, Phys. Med. Biol., Apr. 21, 2009, p. N167-N176, vol. 54, Physics in Medicine and Biology, IOP Publishing.

(Continued)

*Primary Examiner* — David Porta
*Assistant Examiner* — Kenneth J Malkowski
(74) *Attorney, Agent, or Firm* — Da Vinci Partners LLC; John Moetteli

(57) ABSTRACT

A quality control accessory (QC accessory) is provided which is adapted for use in linear accelerator quality control or in verification of an arbitrary isocentric radiation treatment plan of a patient or radiation sensitive body. The accessory includes an absorber, a detector and an optional orientation device. The absorber is rotationally symmetric, preferably spherical or hemispherical. The detector is adapted to be fixed in a stationary spatial relationship with respect to the absorber. The optional orientation device is adapted to maintain the two dimensional detector (2d detector) and the absorber in a fixed relative spatial relationship with respect to the beam focus of the linear accelerator, when the gantry is rotated, so that the central axis of the beam is essentially orthogonal to the 2d detector and the phantom axis of symmetry is parallel to or aligned with the central axis of the gantry rotation axis.

23 Claims, 14 Drawing Sheets

(56) References Cited

OTHER PUBLICATIONS

Häring et al., Hochauflösende 3D IMRT Verifikation mit einem Ionisationskammerarry, Tagungsband, 37. Jahrestagung der Deutschen Gesellschaft für Medizinische Physik e.V., Sep. 20-23, 2006, Regensburg.

Rhein et al., Dosimetrische Verifikation von IMRT-Gesamtplänen am Deutschen Krebsforschungszentrum Heidelberg, Z. Med. Phys., 2002, p. 122-132, vol. 12.

Schiefer et al., Prüfung und Kalibration der MLC-Positionierung mit einem portalen Bildgebungssystem, Z. Med. Phys., 2008, p. 51-58, vol. 18.

Low et al., Phantoms for IMRT Dose Distribution Measurement and Treatment Verification, Int. J. Radiation Oncology Biol. Phys., 1998, p. 1231-1235, vol. 40, No. 5.

Schiefer et al., The Swiss IMRT dosimetry intercomparison using a thorax phantom, Med. Phys., Aug. 2010, p. 4424-4431, vol. 37, No. 8.

International Search Report, International patent application No. PCT/IB2011/000224, Jul. 29, 2011.

* cited by examiner

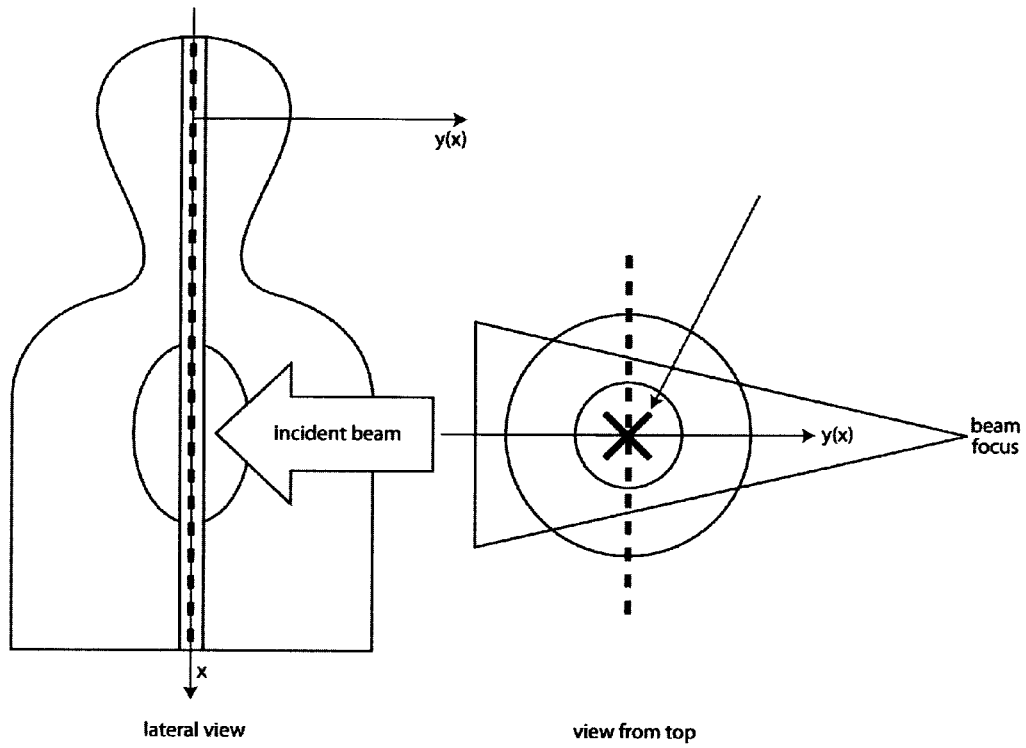
lateral view
view from top
FIG. 13A
FIG. 13B
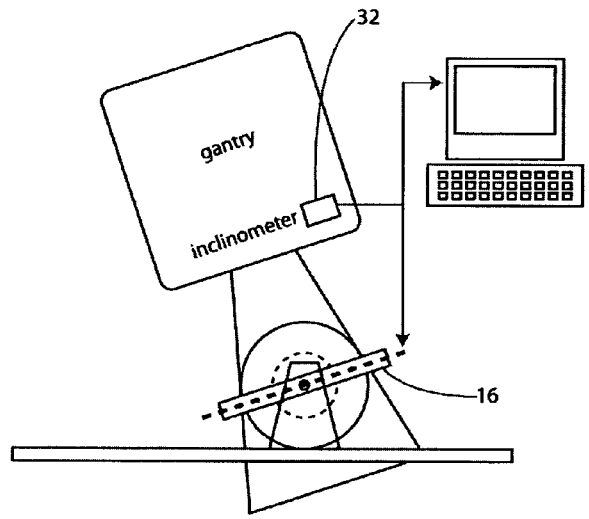
FIG. 14

FIG. 17A 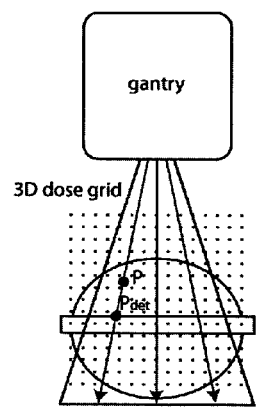 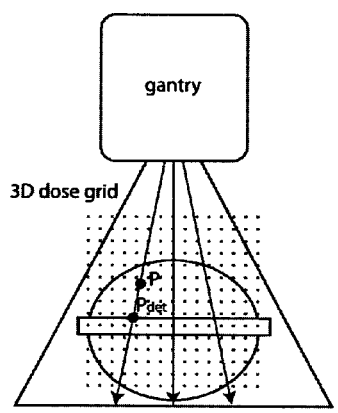 FIG. 17B

FIG. 25
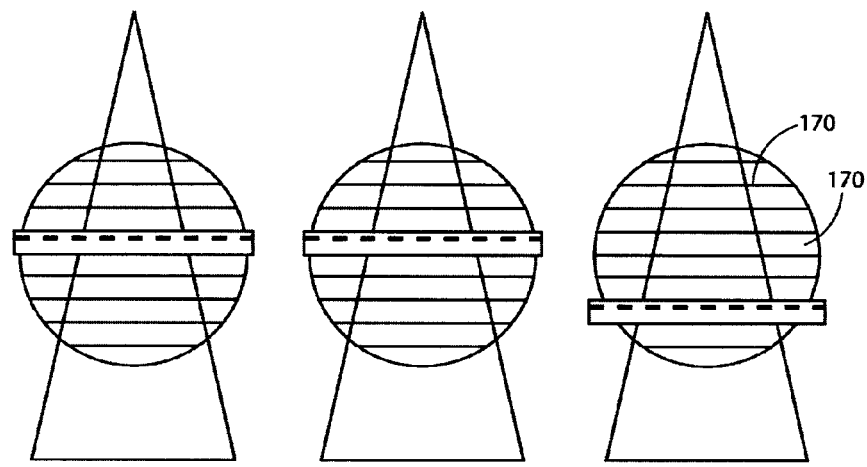
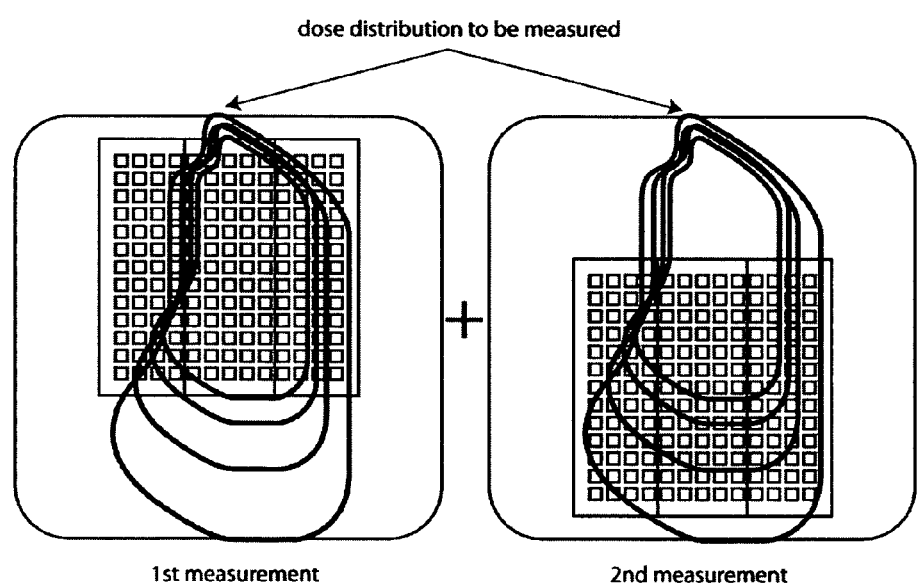
FIG. 26

ROTATIONALLY SYMMETRICAL COHERENT VERIFICATION PHANTOM (VIRTUAL PATIENT) WITH A FLAT DETECTOR DISPOSED ON A ROTARY AXIS INTEGRATED IN A MULTI PURPOSE QC-ACCESSORY

CROSS REFERENCE TO RELATED APPLICATIONS

This application is the National Stage of International Application No. PCT/IB2011/000224, filed Feb. 9, 2011, which claims benefit under 35 USC §119(a), to provisional US patent application Ser. No. 61/302,550 filed Feb. 9, 2010, provisional U.S. patent application Ser. No. 61/412,407, filed Nov. 11, 2010 and provisional U.S. patent application Ser. No. 61/418,439, filed Dec. 1, 2010.

COPYRIGHT & LEGAL NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. Further, no references to third party patents or articles made herein is to be construed as an admission that the present Invention is not entitled to antedate such material by virtue of prior Invention.

FIELD OF THE INVENTION

The invention is a Radiation Oncology QC device, in particular, an instrument for verification of the three-dimensional (3D) dose distribution of patient treatment and for various linear accelerator checks.

BACKGROUND OF THE INVENTION

Before a tumor patient is irradiated, the calculated dose distribution of the treatment plan has to be checked. Since the measurements cannot be performed in the patient himself, phantoms are used. The dose distribution can be checked by recalculating the treatment plan for a "verification phantom". The measured dose distribution of one or various randomly selected layers in the verification phantom is compared with the calculated dose distribution (plan related verification). Alternatively, the dose distribution of each single field is calculated and measured (field related verification). The advantages and disadvantages of these verification methods have been discussed in detail in the medical physics literature. In the current practice of radio oncology clinics, the dose distribution is checked only randomly and in two dimensions (2D).

The 2D dose distribution can be measured with a variety of devices such as films or electronic 2D arrays and EPIDs (Electronic Portal Imaging Device). The latter equipments show the advantage to make available the measured values in an electronic form. Several companies offer electronic 2D arrays and appropriate software, to verify the radiation dose distribution in a plane of special interest. The company Varian introduced a practical tool on the market, which is routinely used in many institutions for field-related 2D verification. 3D verification methods allow checking the integral dose distribution within a volume of interest. Relevant structures (body contour, anatomical structures, the planning target volume, PTV, and critical organs) and the dose distribution can be superimposed on the 3D dose distribution. By this means, evaluations and statements regarding the integral agreement between measurements and calculations are achievable, e.g., presented as a structure-based "Gamma-volume" diagram [Low et al., 1998, A technique for the quantitative evaluation of dose distributions, full cite, the content of which is incorporated herein by reference thereto]. Discrepancies between measurement and calculation can be localized and scored relative to the patient contours. Deviations outside the body contour are for instance not relevant.

Different methods have been developed to measure the 3D dose distribution in a phantom (gel dosimetry, a spirally wounded film in a phantom and mathematical estimation of doses in points outside the measurement plane. These methods are quite elaborate and time-consuming and therefore not suitable for clinical routine: First of all, the 2D measurement signal has to be converted digitally (e.g., film scanning). To convert the measured values into a radiation dose, a conversion function has to be determined, etc. Various groups succeeded in determining the 3D dose distribution, based on EPID measurements. As this equipment is attached to the linear accelerator and has a high spatial resolution, it offers significant advantages compared with other equipment. The industry has not adopted and implemented until now the 3D dose verification with EPIDs.

New products are currently on the market which determine the 3D dose distribution in a phantom based on 2D measurements. As an example, the verification phantoms "Delta4" (available from Scandidos Inc.) and "ArcCheck" (Sun Nuclear Inc.) are presented here.

The cylindrical instrument "Delta4" (IBA) incorporates two 2D detectors, which intersect in the phantom symmetry axis by 90°. The dose distribution outside the measurement planes is calculated. The beam impinges on the detectors partly at small angles, influencing the sensitivity in an adverse way, and limiting the number of detector elements suitable for measurements. (FIG. 1A). The detectors of the cylindrical "ArcCheck" (Sun Nuclear) phantom are located regularly on a cylinder shape below the phantom surface. Detectors next to the phantom symmetry axis (seen from the beam focus) are irradiated perpendicularly and show good measurement results. However, when the angle between the incident beam and the phantom symmetry axis is increased, the incident angle of the beam to the detectors decreases. Therefore, detectors at the peripheries of the phantom are only suitable for measurements when the sensitivity is angle corrected (FIG. 1B), which introduces an additional measurement error. A considerable percentage of the detectors thus cannot be used for the measurement without restrictions at a given gantry angle. The dose within the curved, closed measurement surface is set in relation to the measured dose at the detector positions. This gives information how to calculate the "measured" dose derived from the calculated one.

The Compass measurement system (IBA dosimetry): The 2D array detector is attached to the gantry and measures the field fluence (not the radiation dose). Since the measurement is performed distant to the isocenter plane, complex calculation algorithms are required to calculate the dose in a virtual 3D phantom.

As shown in FIG. 1A, the beam path is perpendicular to the detector plane 1. It delivers a well-defined measurement signal. For the detector plane 2, the opposite is true. In FIG. 1B, the beam path c is perpendicular to the detector plane on the entrance and exit side of the beam and therefore a well measurement signal is expected. For the beam path b, the opposite is true.

Due to the phantom construction of the presented 3D verification phantoms and the limited accuracy to place them in relation to the beam coordinate system, the 3D phantoms actually in use are not suitable to perform fast and accurate machine checks, especially for MLC checks (multi leaf collimator). What is needed therefore is a phantom construction that is reproducibly related to the beam coordinate system with its accessory holder. Further, what is needed is a QC accessory that is more universally applicable.

Towards this end, Häring et al presented a particular member of the RSC Phantom class. (See Häring et al., "Hochauflösende 3D IMRT Verifikation mit einem Ionisationskammerarray", Proceedings of the 39th Annual Meeting of the DGMP, Oldenburg, p. 222-223, 2008, the content of which is incorporated by reference in.). Häring et al used a semicylindrical phantom body. Nevertheless, Häring et al's efforts highlighted problems in calculating the dose distribution, particularly, next to the phantom surface. Cylindrical phantom shapes are therefore not suitable to verify techniques with varying collimator or table angles, when they are fixed to the gantry. What is needed therefore is a phantom class that is suitable for such purpose.

SUMMARY OF THE INVENTION

A quality control accessory (QC accessory) is provided which is adapted for use in linear accelerator quality control or in verification of an arbitrary isocentric radiation treatment plan of a patient or radiation sensitive body. The accessory includes an absorber, a detector and an optional orientation device. The absorber is rotationally symmetric, preferably hemispherical or spherical. The detector is typically planar and 2 dimensional, although when used herein, the use of the term 2d detector is meant to include the plurality as well as a 3d detector matrix which is essentially a stacking of 2d detectors. The detector is adapted to be fixed in a stationary spatial relationship with respect to the absorber. The optional orientation device is adapted to maintain the two dimensional detector (2d detector) and the absorber in a fixed relative spatial relationship with respect to the beam focus of the linear accelerator, when the gantry is rotated, so that the central axis of the beam is essentially orthogonal to the 2d detector and the phantom axis of symmetry is parallel to or aligned with the central axis of the gantry rotation axis.

The QC accessory (quality control accessory) consists in principal of three components: The gantry fixation accessory holder, the phantom body or absorber, and the 2D array. Software is needed to interpret the measurement.

Verification Phantom Component of the QC Accessory

The plan verification phantom as part of a general class of 3D phantoms is the most important component of the QC accessory. Members of the here presented class are called "Rotationally Symmetrical Coherent" phantoms (RSC phantoms). As indicated by the name, RSC phantoms are rotationally symmetric to an axis. A 2D array is placed in the diameter plane of the phantom. Thus, the symmetry axis of the phantom lies in the 2D array measurement plane.

The symmetry axis of the RSC phantoms coincides with the gantry rotation axis. The 2D array is aligned to the isocenter line of the incident beam by turning the phantom around its symmetry axis, in order that the central beam impinges perpendicularly on the detector surface. The alignment of the phantom to the gantry can be achieved in different ways (see later). The favorable and most simple method is realized when the phantom is mounted on the gantry with a dedicated accessory system; with the same fixation technique as applied for the block tray accessory (photon beams) or the electron tube accessory (electron beams). The flexibility can be realized by switching the accessory coding system. Alternatively, the linac software provides an accessory code for photon as well as for electron beams.

Due to the properties mentioned above, RSC phantoms are "coherent": Since the relative orientation of the impinging beam to the 2D array does not depend on the gantry angle, the sensitivity of each detector element does not depend on the gantry orientation. Due to the rotational symmetry of the phantom, viewed from the room coordinate system, the applied dose distribution does not change when the phantom is rotated around its symmetry axis.

The phantom consists of a phantom body, an accessory fixed to the gantry, a 2D array and (when the spatial information is not provided by the steering software of the linac itself) a measurement device to define the spatial orientation of the gantry, the collimator, the table and/or the 2D array. Software is required to transform the 2D measurement information from the 2D array into a 3D dose distribution in the RSC phantom and finally into the "measured" dose distribution in the patient anatomy shown in CT slices.

Solutions are presented to solve detailed problems in the actual context. They are a feature of the invention.

In the patent application presented here, the Phantom class is considered in general terms, including possible variants. The variants are created by varying the rotationally symmetrical phantom body and/or the measurement geometry. It is pointed out how these variations can be considered mathematically or compensated by measurements. In addition, a dose calculation algorithm is presented. It is based on simple rules, making use of the simple phantom and measurement geometry. The simple measurement geometry is made possible because of the (symmetrically) fixed position of the beam focus relative to the symmetry axis of the phantom body. It avoids the disadvantages mentioned by Haring et al. The algorithm and its components are considered as a feature of the invention.

Spherical phantoms of different diameters and point symmetrical density distribution are the most flexible and therefore most important members of the RSC phantom class. They are suitable to verify any type of isocentric irradiation technique with arbitrary collimator (rotational IMRT with varying collimator angles < >0°) or table angles (non-coplanar irradiation techniques). They are a feature of the invention. In contrast, cylindrical phantom shapes are not suitable to verify techniques with varying collimator or table angles, when they are fixed to the gantry. The following presentation is done on the basis of spherical phantom bodies which are fixed to the gantry.

Machine QC Component of the QC Accessory

Due to the fixed and reproducible position of the 2D array relative to the beam coordinate system, a repeated calibration of the phantom (2D array) position in the beam coordinate system is not needed prior to the measurements.

This allows performing some machine checks very rapidly without loss of accuracy. The phantom body is replaced by other absorbers which fit to the measurement parameter of actual interest. Measurement techniques for different machine parameters are described in the literature and are therefore not a feature of the invention. They include:

absolute measurement of the collimator and MLC positions in the beam coordinate system
  determination of different beam parameters: energy, symmetry and homogeneity, dose (when the 2D array is stable in time under consideration of temperature and air pressure - - - note, that due to the encoding of the QC accessory, these checks can be performed for photon as well for electron beams).

These measurements are supported independent of the gantry and collimator angles without loss of accuracy. The novel concept of an accessory based combination of 3D plan verification and machine checks is a feature of the invention.

The QC accessory of the invention is mountable to the gantry similar to the block tray or the electron tube accessory. The QC accessory may be considered a component of the linear accelerator. It consists first of a new class of 3D verification absorbers or phantoms. Members of this class are called "Rotationally Symmetrical Coherent" phantoms (RSC phantoms). The most important phantom body shows a (semi) spherical shape. A 2D detector array is placed in the diameter plane of the phantom. The symmetry axis of the phantom coincides with the gantry rotation axis. Due to the fixed position of the phantom relative to the gantry, the beam isocenter line is always orthogonal to the 2D array. The phantom is therefore "coherent". The orientation of the impinging beam is determined with suitable measurement devices (inclinometers, gyroscopes, gyrometers 32), which are integrated in the phantom or connected to it. A dose calculation algorithm has been developed to define the 3D dose distribution, derived from the 2D measurement. The 3D dose distribution is transferred to the patient anatomy, which allows applying the most widespread evaluation methods in the clinical routine. An additional application 2 of the QC accessory is focused on measurements of machine or beam parameters of general interest. The accessory is suitable for photon and for electron beams.

It is an object of the invention to provide a class of phantoms whose use is suitable to all detectors for reliable measurements, independent of the gantry angle and site of the incident beam.

BRIEF DESCRIPTION OF THE DRAWING(S)

FIGS. 13A and 13B are front and top views, respectively, illustrating how the general shape and density distribution of a RSC phantom can differ strongly from a cylindrical one.

FIG. 14 is a schematic view showing the phantom placed on the treatment table.

FIGS. 17A and 17B are schematic views illustrating the dose distribution of a large irradiation field (hereinafter, designated as a "flood field"), which covers the entire phantom.

FIG. 25 is a series of front views showing a measurement method for measuring the 2d dose distribution in the inside of the phantom FIG. 26 is a schematic diagram showing how composite measurements of a large 3D dose distribution can be obtained using the invention.

Those skilled in the art will appreciate that elements in the Figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. The drawings show examples of one of several possible means of implementing the QC accessory of the invention, which is independent on the linac manufacturer and model. The drawings show therefore only general ideas and are not true to scale. For different manufacturers, multiple solutions are possible. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT(S)

The QC accessory 10 (quality control accessory) consists in principal of three components: The gantry fixation accessory holder, the phantom body 30 or absorber 12, and the 2D array 14. Software is needed to interpret the measurement.

Figure 1A:
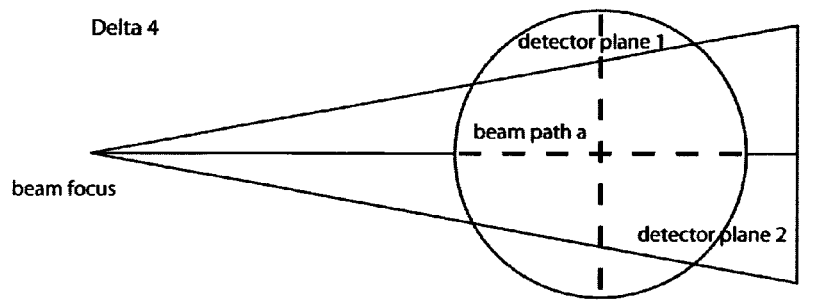
FIG. 1A is a schematic drawing showing the beam path perpendicular and parallel to the detector planes 1 and 2, respectively.
Figure 1B:
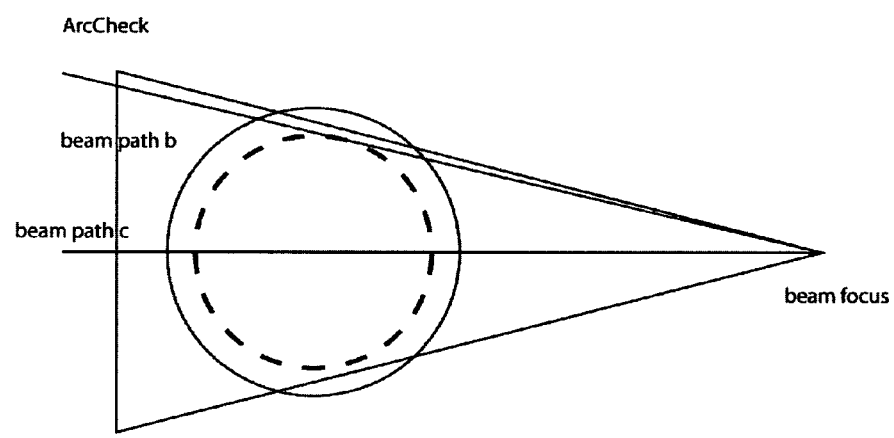
FIG. 1B is a schematic drawing showing the beam path impinging on a cylinder.
Figure 2:
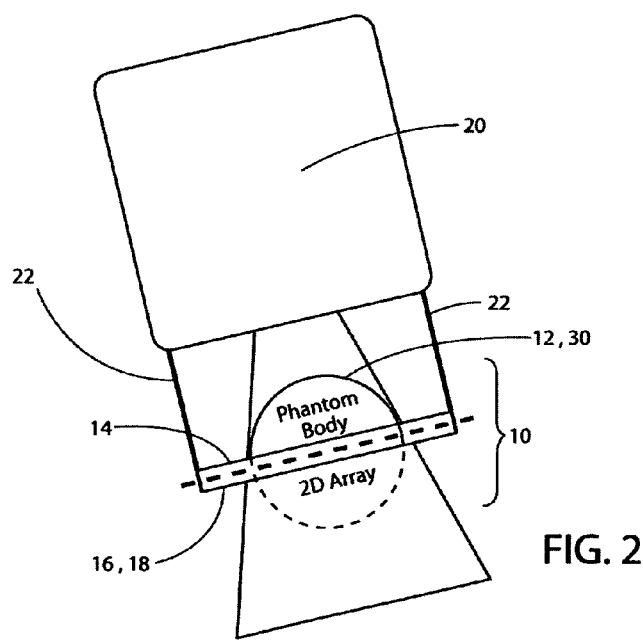
FIG. 2 is a schematic drawing of the QC accessory of the invention used in verification of 3D dose distribution.

Referring now to FIG. 2, components of the QC accessory 10 are shown used in verification of 3D dose distribution. The QC accessory 10 includes an absorber 12 (in this case, a phantom 12, 32), and a 2d array 14 which is adapted to be fixed on a table 16 or collimator 18 which is held in a fixed spatial relationship to the gantry 20 by an orientation device 22 (in this case, a rigid structure).

Verification Phantom Component of the QC Accessory

The plan verification phantom as part of a general class of 3D phantoms is the most important component of the QC accessory 10. Members of the class of phantoms of the invention are called "Rotationally Symmetrical Coherent" phantoms (RSC phantoms). As indicated by the name, RSC phantoms are rotationally symmetric to an axis. A 2D array 14 is placed in the diameter plane 112 of the phantom. Thus, the symmetry axis of the phantom lies in the 2D array measurement plane 106.

The symmetry axis of a RSC phantom coincides with the gantry rotation axis. The 2D array 14 is aligned to the isocenter line of the incident beam 26 by turning the phantom around its symmetry axis, in order that the central beam impinges perpendicularly on the detector surface. The alignment of the phantom to the gantry 20 can be achieved in different ways (as described later). The favorable and most simple method is realized when the phantom is mounted on the gantry 20 with a dedicated accessory system; with the same fixation technique as applied for the block tray accessory (photon beams) or the electron tube accessory (electron beams). The flexibility can be realized by switching the accessory coding system. Alternatively, the linac software provides an accessory code for photon as well as for electron beams.

Due to the properties mentioned above, RSC phantoms are "coherent": Since the relative orientation of the impinging beam to the 2D array 14 does not depend on the gantry angle, the sensitivity of each detector element does not depend on the gantry 20 orientation. Due to the rotational symmetry of the phantom, viewed from the room coordinate system, the applied dose distribution does not change when the phantom is rotated around its symmetry axis.

Figure 3:
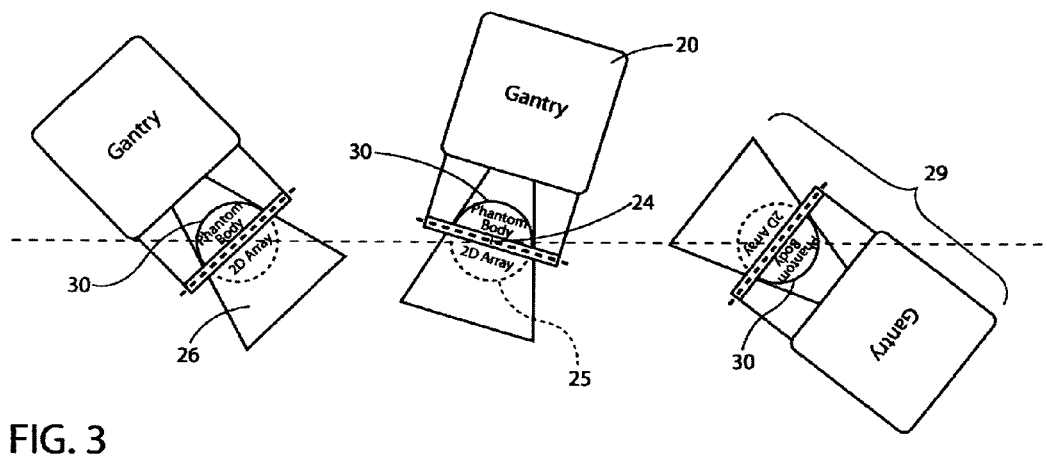
FIG. 3 shows three snapshots of gantry, phantom and table orientation during rotation of the gantry, illustrating the principle of the dose verification with a spherical RSC phantom.

Referring now to FIG. 3, the principle of the dose verification with a spherical RSC phantom 30 is shown by way of three snapshots of the Gantry and QC accessory assembly 29 at differing gantry angles. When the gantry 20, the collimator 18 (and/or the table 16) are rotated around the isocenter point 24, the outline 25 of the spherical phantom body 30 is not shifted. The 2D array 14 is oriented always with the central axis of the incident beam 26.

The QC accessory 10 is made up of a phantom 12, a structure 22 fixed to the gantry 20, a 2D array 14 and (when the spatial information is not provided by the steering software of the linac itself) a measurement device (such as a gyroscope or an inclinometer 32) capable of determining the spatial orientation of the gantry 20, the collimator 18, the table 16 and/or the 2D array 14. Software is required to transform the 2D measurement information from the 2D array 14 into a 3D dose distribution in the RSC phantom and finally into the "measured" dose distribution in the patient anatomy shown in CT slices.

Solutions are presented to solve detailed problems in the actual context. They are a feature of the invention.

In the instant patent application, the Phantom class is considered in general terms, including possible variants. The variants are created by varying the rotationally symmetrical phantom body and/or the measurement geometry. It is pointed out how these variations can be considered mathematically or compensated by measurements. In addition, a dose calculation algorithm is presented. It is based on simple rules, making use of the simple phantom and measurement geometry. The simple measurement geometry is made possible because of the (symmetrically) fixed position of the beam focus relative to the symmetry axis of the phantom body 30. It avoids the disadvantages mentioned by Häring et al. The algorithm and its components are considered as a feature of the invention.

Spherical phantoms of different diameters and point symmetrical density distribution are the most flexible and therefore most important members of the RSC phantom class. They are suitable to verify any type of isocentric irradiation technique with arbitrary collimator (rotational IMRT with varying collimator angles < >0° or table angles (non-coplanar irradiation techniques). They are a feature of the invention. In contrast, cylindrical phantom shapes are not suitable to verify techniques with varying collimator 18 or table angles, when they are fixed to the gantry 20. The following presentation is done on the basis of spherical phantom bodies which are fixed to the gantry 20.

Machine QC Component of the QC Accessory

Due to the fixed and reproducible position of the 2D array 14 (or a known configuration) relative to the beam coordinate system 34, a repeated calibration of the phantom (or 2D array 14) position in the beam coordinate system 34 is not needed prior to the measurements.

Figure 4A:
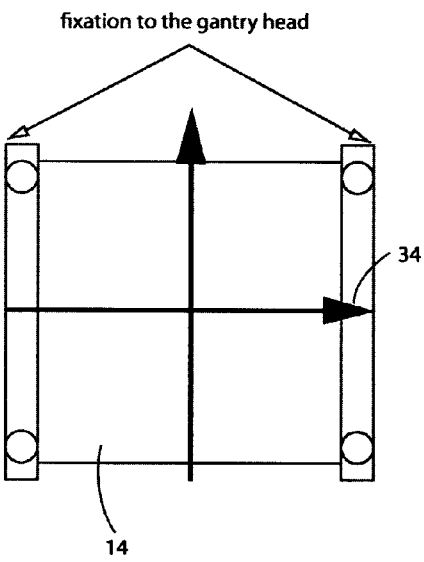
FIG. 4A is a plan view of the gantry fixation system.
Figure 4B:
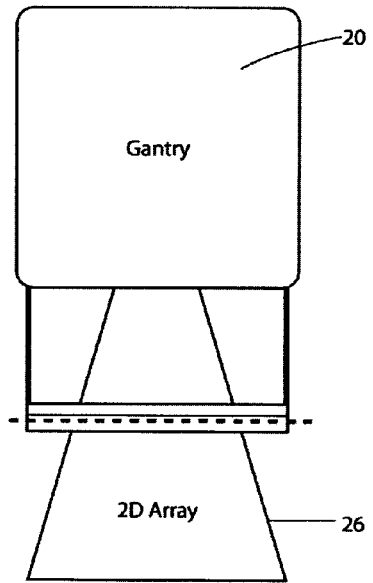
FIG. 4B is a front view of the gantry, table and fixation system.

Referring now to FIGS. 4A and 4B, the 2D array 14 is interchangeably but reproducibly fixed to the beam coordinate system 34. This allows performing certain machine checks very rapidly without loss of accuracy. The phantom body 30 is replaced by other absorbers 12 which fit to the measurement parameter of actual interest. Measurement techniques for different machine parameters are described in the literature and are therefore known in the art. They include (1) absolute measurement of the collimator 18 and MLC positions in the beam coordinate system 34, and (2) determination of different beam parameters: energy, symmetry and homogeneity, dose (when the 2D array 14 is stable in time under consideration of temperature and air pressure).

Due to the encoding of the QC accessory 10, these checks can be performed for photon as well for electron beams. These measurements are supported independent of the gantry and collimator angles without loss of accuracy.

Construction and Principle of Coherent Rotation Phantoms

The following descriptions are not intended to limit the scope of the Invention in any way as they are exemplary in nature and serve to describe the best mode of the Invention known to the inventor as of the filing date hereof. Consequently, changes may be made in the arrangement and/or function of any of the elements described in the disclosed exemplary embodiments without departing from the spirit and scope of the Invention.

Figure 5:
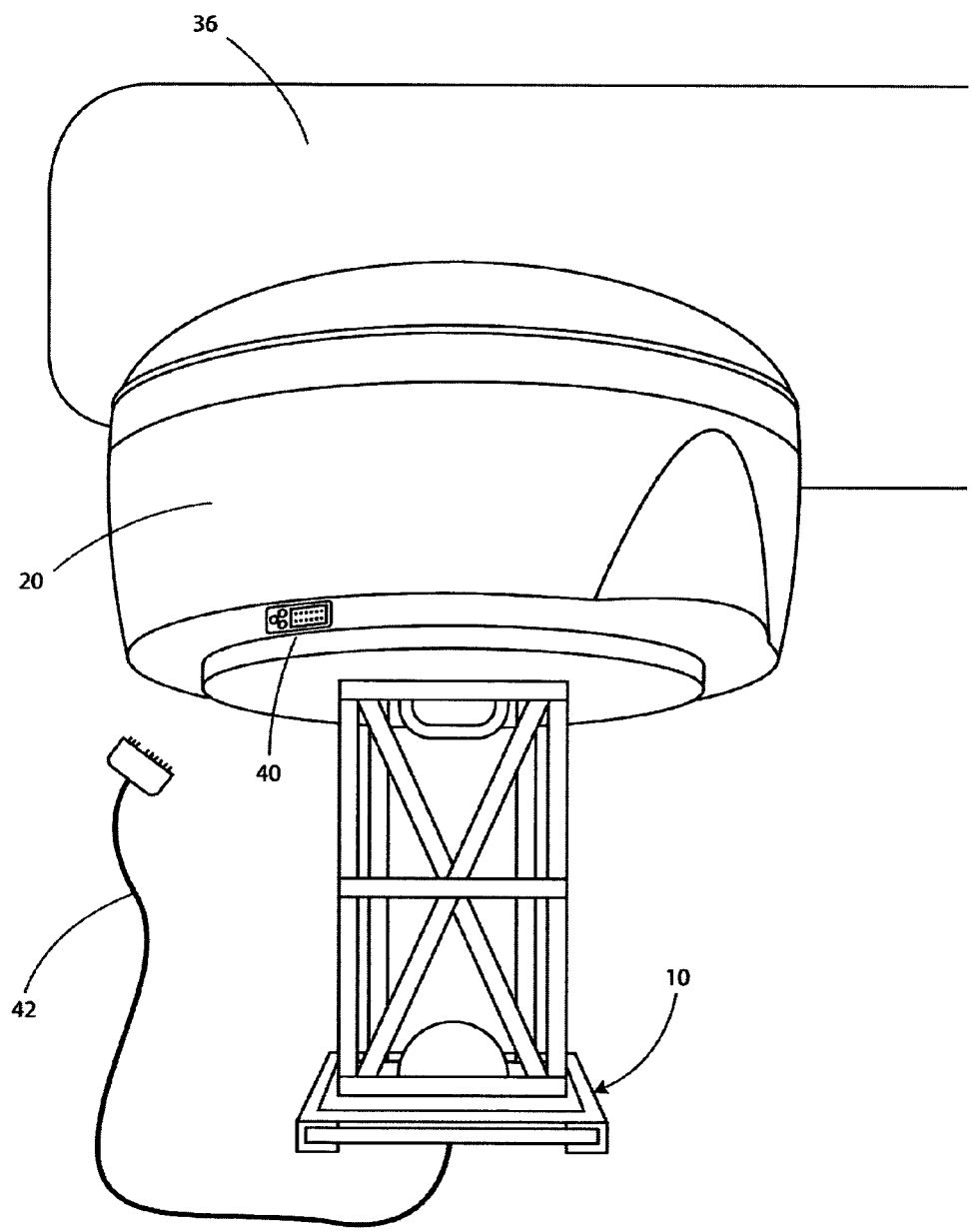
FIG. 5 is a perspective view of the QC accessory of the invention attached to the gantry.

Referring now to FIG. 5, the QC accessory 10 of the invention is attached to the gantry 20 (which is part of the linac 36). The linac 36 is provided with a data and/or power supply connector 40. The table 16 preferably includes a data or power cable 42 which connects to the connector 40.

Figure 6:
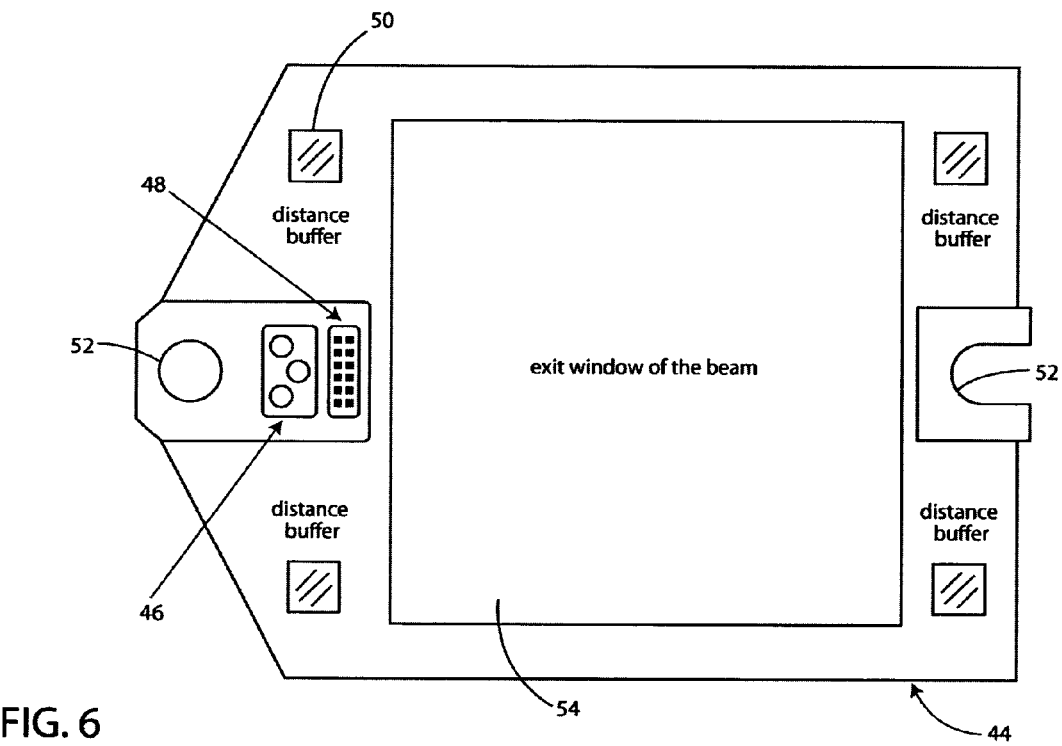
FIG. 6 is a plan view of a typical means of fixation of the QC accessory holder of the invention to the gantry.

Referring now to FIG. 6, a typical means of fixation 44 of the QC accessory 10 holder of the invention to the gantry 20 is shown. Here, a data cable 48 is provided for accessory encoding, necessary to deal with electron beams, photons, and data transfer from the 2D array 14. A power supply connection 46 is provided where the accessory 10 is not powered by a battery. Fixing means 52 are provided for fixing the fixation 44 to braces 56. The exit window 54 of the beam is located in the center of the fixation 44.

Here, the fixation plate 44 of the QC accessory 10 is seen from the focus point. This model is particularly useful with Elekta Synergy linacs, as an example. The accessory holder 44 shown here has integrated a power supply and data connection 46 and 48, respectively, to the gantry 20. Other connections are possible. In a variant, the 2D array 14 is connected to a power supply and data connection integrated elsewhere in the gantry 20.

Figure 7:
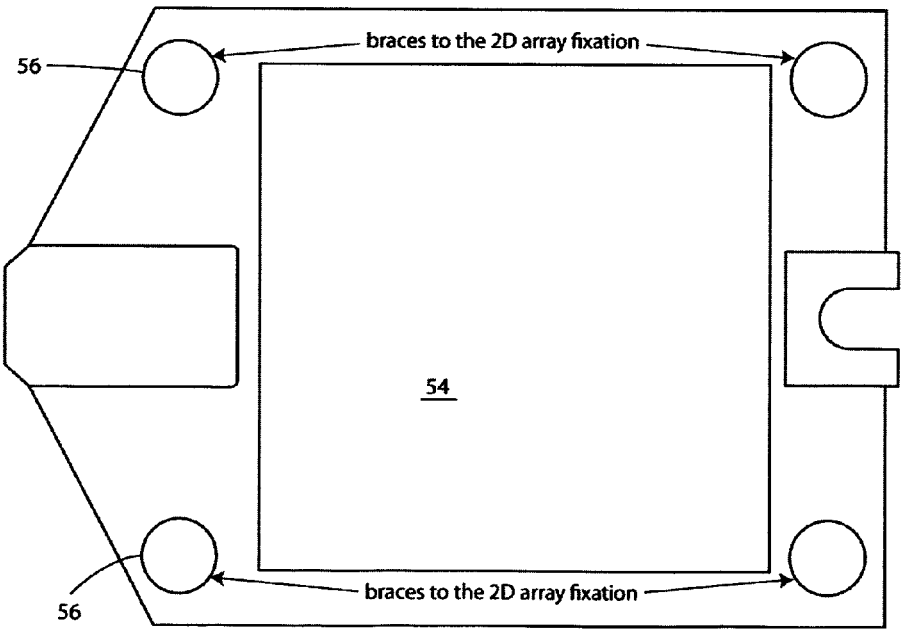
FIG. 7 is view of the fixation plate of the QC accessory as seen from the isocenter point

Referring now to FIG. 7, the fixation plate 44 of the QC accessory 10 is shown from the isocenter point 24. Here, braces 52, 56 are shown which attach to the fixation 60 of the 2D array 14. These braces 56 fix the 2d array and the phantom in the isocenter point (in the center of the sphere). They correspond to the fixation 72 in FIGS. 10A and 10B.

3. QC Accessory Holder with the Mounted 2D Array

Figure 8:
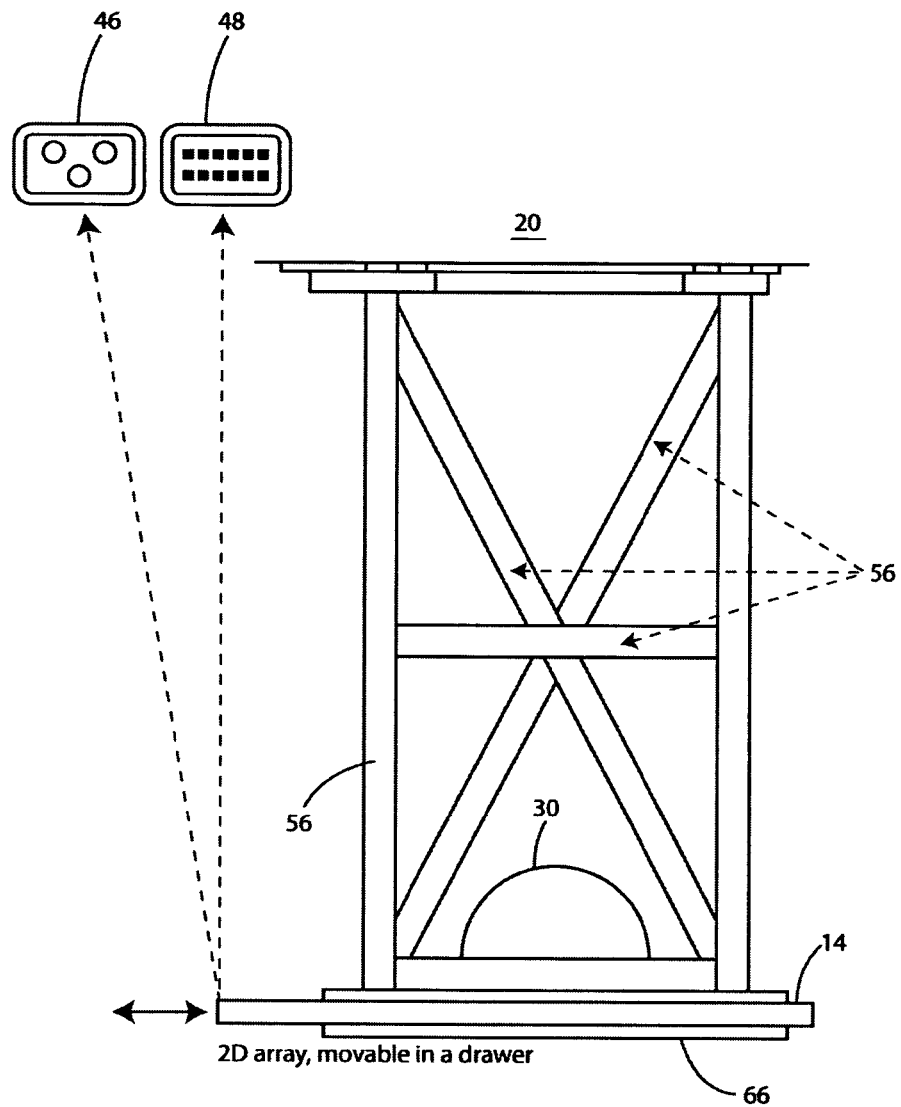
FIG. 8 is a lateral view of the QC accessory holder of the invention.

Referring to FIG. 8, a lateral view to the QC accessory 10 holder of the invention is shown. Braces 56 are attached between the gantry 20 and the fixation 44, which in turn holds the QC accessory 10. Power supply 46 and data connections 48 may be integrated into the accessory holder 44 or in the gantry 20. The 2D array 14 can be disposed in a sliding drawer 66. This is essential for large or asymmetrical fields.

Figure 9:
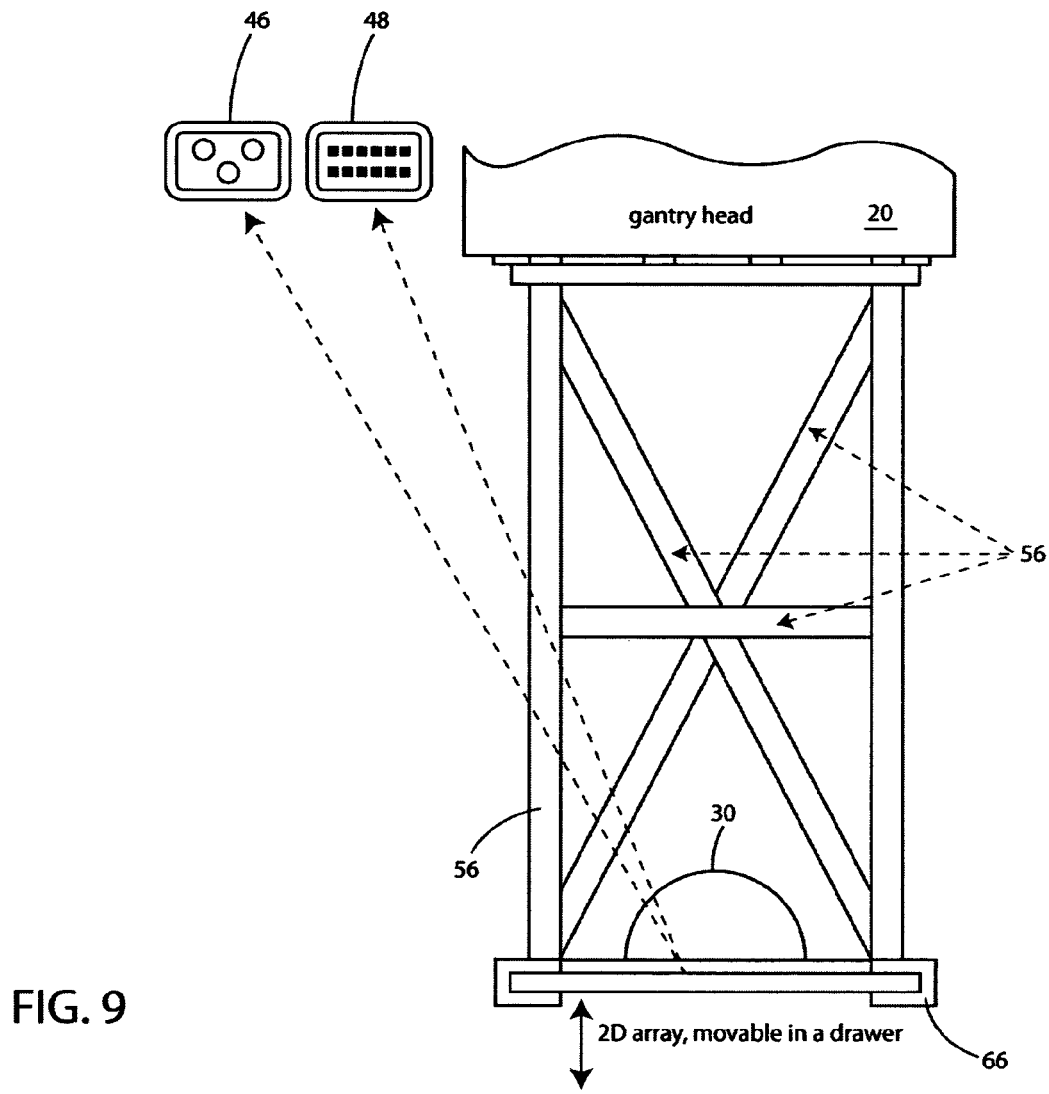
FIG. 9 is a front view of the QC accessory holder of the invention.

Referring now to FIG. 9, a frontal view to the QC accessory 10 holder of the invention is shown. Here, the drawer 66 into which the 2D array 14 slides is more clearly shown.

4. Fixation of the Phantom Body on the 2D Array with a Base Plate.

The phantom base plate 70 and therefore the fixation 72 to the QC accessory 10 is the same for all phantom shapes. The base plate 70 does change the scatter only slightly, which is taken into account by the calculation algorithm. The 2D array 14 is provided with drillings to fix the base plate 70. Other fixations are possible.

Figures 10A, 10B:
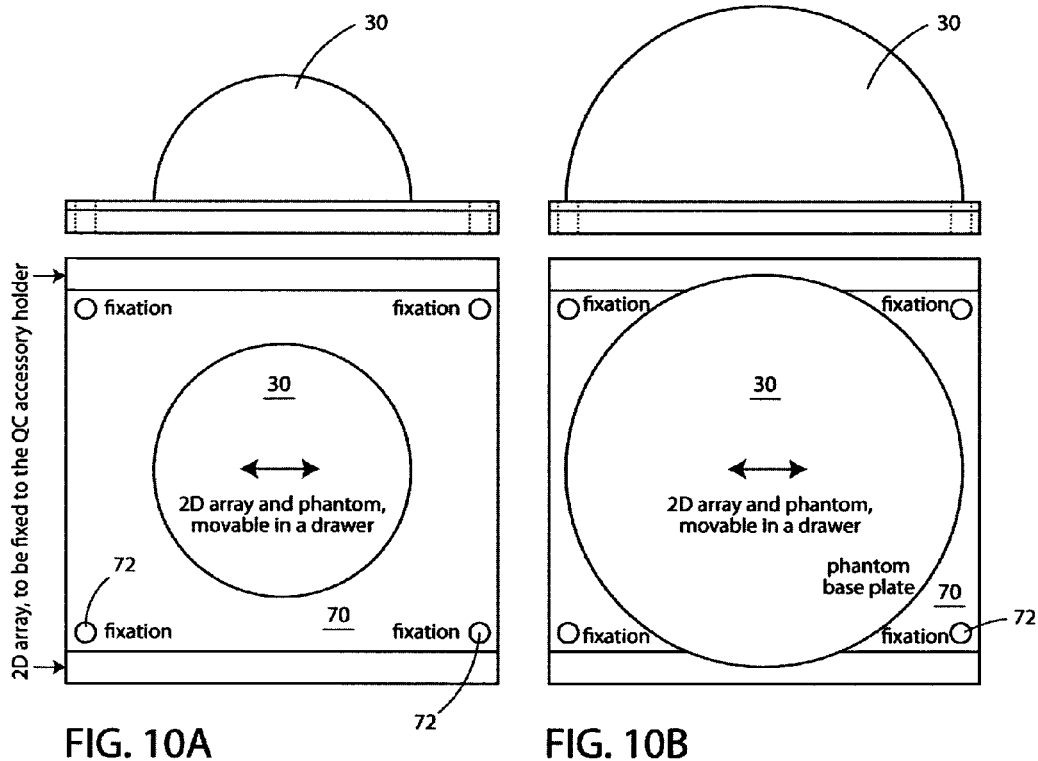
FIGS. 10A and 10B are schematic plan and side views, showing phantom bodies of different sizes but using an identical base plate which is fixed permanently to the phantom body.

Referring now to FIGS. 10A and 10B, phantoms 12 of different sizes are shown using using an identical base plate 70 fixed permanently to the phantom body 30. Fixations 72 attach the phantoms 12 via the base plates 70 thereof, to the accessory holder 44 and/or to the 2D array 14.

5. Electron Frame

Figure 11A:
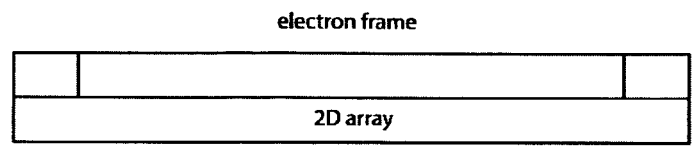
FIG. 11A is a side view of the electron frame, shown without a base plate, fixed to the 2D array similar to a phantom bodies and absorbers.
Figure 11B:
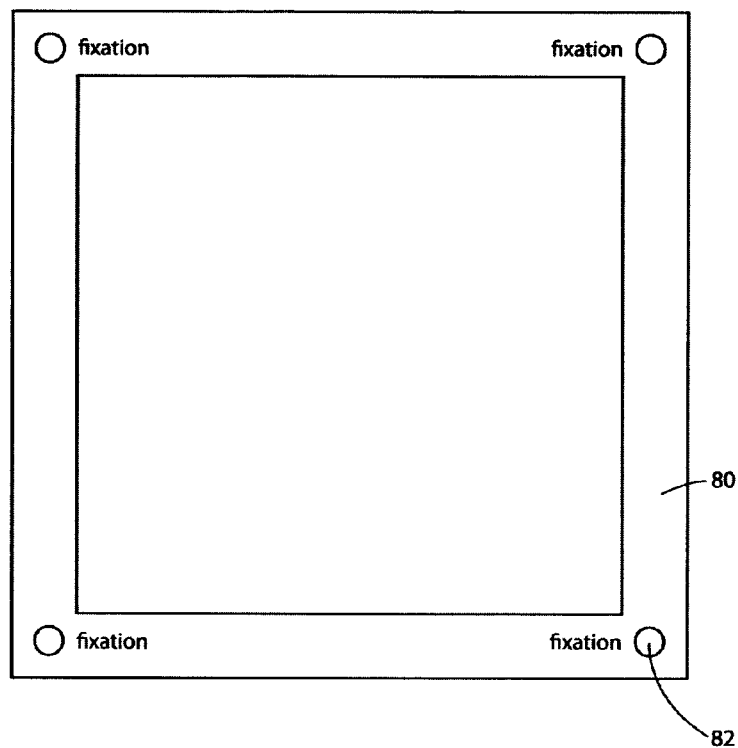
FIG. 11B is a top view of the electron frame fixed to the 2D array similar to a phantom bodies and absorbers.

Referring now to FIGS. 11A (lateral view) and 11B (front view seen from the beam focus) the electron frame 80 is fixed to the 2D array 14 similar to a phantoms and absorbers 12. It consists on high Z material (lead . . . ). When the fixation 82 is positioned on the blocking frame (not shown but known in the art), a base plate 70 is not needed. The need of a base plate 70 depends on the electron energy to be tested. Therefore a mixed technique (low energies without a base plate 70, higher energies with a base plate) can be preferable. It should be mentioned that the 2D array 14 itself can have some buildup material integrated to it which may influence the need of a base plate 70 under certain circumstances. Here the Electron frame 80 is shown without a base plate.

Measurement Principle

Figure 12:
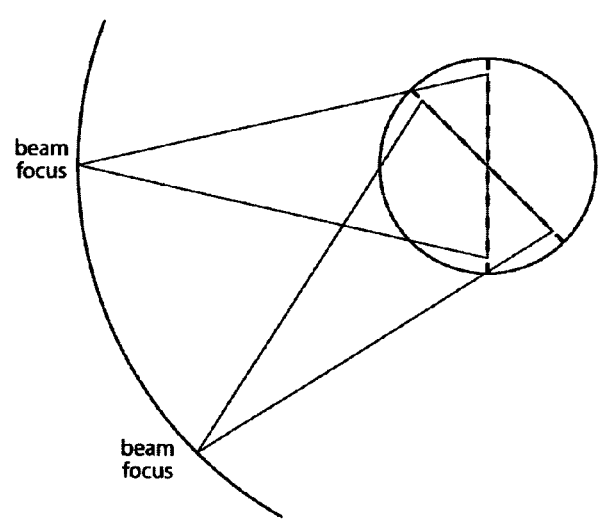
FIG. 12 is a schematic view showing a rotationally symmetrical (RSC) phantom with different incident beam directions and detector orientations.

Referring to FIG. 12, a rotationally symmetrical (RSC) phantom is shown with different incident beam directions and detector orientations. The detector is shown for two different gantry angles.

The symmetry axis is perpendicular to the paper plane and coincides with the rotation axis of the gantry 20, as well as the beam focus. A 2D array 14 lies within the diameter plane 112 of the phantom surface 104.

All detector elements are irradiated almost orthogonal and therefore provide useful measurement results. With a fixed number of detector elements, a higher spatial resolution can be achieved than with other phantom types.

General Shape of RSC Phantom Bodies

Referring now to FIGS. 13A and 13B, the general shape and density distribution of a RSC phantom can differ strongly from the cylindrical one.

Here an RSC phantom, presented in an arbitrary shape: The surface and the density distribution in the inner of the phantom body 30 are defined by any function y(x), see left sketch. They are rotationally symmetric in relation to the x-axis, see right sketch. The 2D array 14 is placed in the central plane (dashed line). Therefore, the symmetry axis is placed in the measurement plane 106.

The phantom body 30 portion on the exit side of the 2D array 14 has rare influence on the measurement and can be omitted. In the following it is therefore not distinguished between full phantoms (showing a 360° rotational symmetry) or halves of it (180° rotational symmetry) and their variants (see later). When the phantom body 30 shows additionally a point symmetry (not only a rotational axis symmetry), it is suitable for irradiation techniques with arbitrary collimator angles and for non-coplanar techniques.

Due to the simple structure of the phantom body 30, a wide variety of materials are suitable for use. For example, PMMA (Polymethylmethacrylate), a transparent thermoplastic or water-equivalent material can be used. Suitable water equivalent materials include "RW3" from PTW AG of Freiburg, Germany, VIRTUAL WATER", available from IRT Associates of Elmsford, USA, "SOLID WATER" available from Gammex Inc, of Middleton, USA, and "PLASTIC WATER" available from CIRS Inc. of Norfolk, USA.

This approach has not been described for the phantom classes and is a feature of the invention application.

In addition to flat 2D arrays 14, curved 2D arrays 14' (one or multiple) can be used. The detector is still aligned to the incident beam 26.

Alignment of the Phantom to the Incident Beam: Implementation

As discussed earlier, the 2D array 14 is at any time oriented to the incident beam 26, in order that the central beam impinges perpendicularly on the detector surface. Due to the symmetry of the phantom body 30, it seems that the phantom has not been rotated. Viewed from the room coordinate system, the applied dose distribution is not affected by the phantom rotation (See FIGS. 3 and 5). Therefore, the dose distribution is measured in a coherent way: The sensitivity of all detector elements is not affected by the gantry angle of the applied beam.

The alignment of the phantom to the incident beam 26 can be realized in various ways, including:

1. The phantom is fixed with a rigid holding device to the gantry 20, see FIGS. 2 and 3. It follows all gantry and collimator rotations and movements and therefore coherence is provided. The holding device is fixed at the same docking station to the gantry 20 as the electron tubes and the block tray system. This method differs from the method presented by Häring et al. and is therefore a feature of the invention. But it isn't a prerequisite for the QC accessory 10 concept. A device is needed to measure geometrical position parameters, see below. Alternatively, the geometrical position is read directly from the linac steering software.
2. The phantom is placed on the table 16. A (motor driven) mechanical device aligns the 2D array 14 with respect to the incident beam angle.

Referring now to FIG. 14, the phantom 12 is placed on the treatment table 16. The 2D array 14 is (motor driven) oriented to the incident beam 26 via a sensor driven controller and motor (not shown). The sensor may be an inclinometer, gyroscope or gyrometer 32. The information of the 2D array 14 and the orientation of the gantry 20 are transferred to the evaluation software.

The table based phantom type is suitable even for arbitrary collimator and table angles, but not for non-coplanar irradiation techniques. Since the measurement accuracy is limited to the accuracy to place the phantom relative to the linac coordinate system, MLC or field size checks cannot be performed with sufficient accuracy. Nevertheless, the motor driven geometrical alignment is a feature of the invention, since it covers the verification part of the QC accessory 10.

The information about the current incident beam angle can be obtained in several ways, i.e.:
- a. A device is mounted on the gantry 20, as seen in FIG. 14. It measures the gantry angle (i.e. an inclinometer, a gyroscope 32 . . . ). The use of a gyroscope for a 3D phantom is a feature of the invention.
- b. The software of the QC accessory 10 has access to the current status of the linac, e.g. by interpreting information from the Record and Verify System or the linac control software.
- c. Using a measurement device that is fixed or placed anywise on the table 16 (or on a device, placed on the table 16) or attached to a component of the phantom, and determines the direction of the incident beam 26.
- d. User input (which is not possible for rotational irradiation techniques).

In terms of a "field-related verification", 3D verification may also be performed with a constant gantry (and collimator) angle. It is simple but not needed to select a 0° gantry angle. In this case the 2D array 14 and the phantom body 30 aren't rotated during the irradiation process. The phantom can, for example, be put on the table 16. A gantry holding device or a motor driven alignment is then not required. The gantry angle, when needed also the collimator and table angles, are then entered manually or read from the DICOM plan file. This option is a feature of the invention. A check of different machine parameters (e.g., MLC positioning, gantry angle, etc.) is not properly supported and reduces the validity of the verification process.

It is assumed in the following that the phantom is attached to the gantry 20. Most considerations and statements (i.e. concerning the scope of the Invention) are still valid for the other options.

Measurement of the Spatial Phantom Orientation

A measurement device to determine the spatial orientation of the gantry 20 and/or the collimator angle (i.e. inclinometer, gyroscope, gyrometer 32 . . . ) in the room coordinate system can be attached to or incorporated in a phantom component (2D array 14, phantom body 30, accessory holder 44) or connected to it. This possibility has not been described in the literature to date, and is a feature of the invention application.

For non coplanar irradiation techniques: An additional device (i.e. a gyroscope) is placed on the table 16 (i.e. in the 2D array interface) and measures the table deflection. The table deflection can be entered alternatively by hand. Häring et at do not consider non-coplanar irradiation techniques or use such measurement devices. The use of these devices in the RSC context is a feature of the invention.

When the collimator angle is <>0° but constant during the treatment, non-hemispherical RSC phantom bodies can be re-rotated by the negative angle in order to align the symmetry axis parallel to the gantry rotational axis. This option is a feature of the invention, independent on the body shape and including cylindrical body shapes.

Exact Position of the 2D Array in the Beam Coordinate System

It is the aim that the 2D array coordinate system coincides with the beam coordinate system 34. Since this cannot be fully achieved with sufficient accuracy, or a displacement is needed when the irradiated volume is placed off axis, the displacement (translation and rotation) of the 2D array coordinate system relative to the beam coordinate system 34 has to be known. Measurements (to be conducted once) are needed to define this relation. Since there are small geometrical differences between various accelerators even for the same model, the calibration has to be performed for each accelerator used in an institution separately. This can be performed in different ways:

Marks 90 (visible or radiation opaque) are drawn or can be placed on the 2D array surface, especially on the bottom and/or front side of the 2D array 14. They indicate the coordinate system of the 2D array measurement plane 106, for example the effective measurement point of the central detector, or an adequate point(s) or line(s) within the 2D array 14; see FIG. 15.

Figure 15:
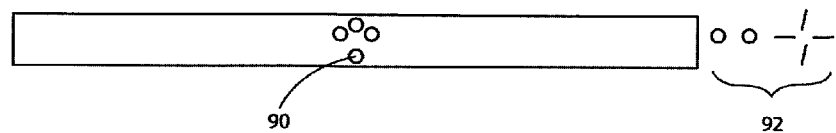
FIG. 15 is a schematic front view of the 2D array showing marks placed thereon.

Referring now to FIG. 15, marks 90 placed on the front of the 2D array 14. Other mark forms are shown as examples to the right of the sketch. The same marks 90 can be used to measure the 2D array 14 position and orientation relative to the gantry and/or collimator rotation axis. 2D array acquisition of a beam with well known geometry, i.e. a regular 10 cm×10 cm field. Evaluation of the detector signals (for example by comparing signals at opposite field edges) allow to define the position and orientation of the 2D array 14 relative to the beam coordinate system 34. The determination of the distance of the measurement plane 106 to the isocenter plane is not included in this measurement but corrected most partly by the calculation algorithm; see below.

Data Transfer from the Measurement Array to the Control Computer

Due to irradiation techniques which require varying collimator and gantry angles, a wire (for instance a RS232 connection) used for the data transfer from the 2D array 14 attached to the gantry 20 to the control computer (or any other measurement equipment which is not a permanent component of the linac, often provided by another manufacturer) is not optimal (but possible in this context). The same is valid for the energy supply. The following options are suitable to solve problems of distorted, embrangled or broken data or voltage cables:

The measurement information collected by the 3D phantom is transferred electromagnetically or by another wave based information transfer technique (i.e. ultrasound; in contrast to a corporal medium like a wire). This differs from the method presented by Häring et al. and is a feature of the invention. (An electromagnetic transfer is state of the art for other measurement equipment, but not in the context of a 3D phantom). The energy supply of the 2D array 14 is provided with a battery, which is plugged to the 2D array 14, the phantom body 30, the gantry holder or to the gantry 20 itself. This differs from the method presented by Häring et al. and is part of the patent.

A data plug 40 is integrated permanently in the gantry 20 (for example for a RS232 connection). The plug forms the end of a wire which is installed in the gantry 20 like other data wires of the gantry 20 (see FIG. 16). It can if any be used for the data transfer of any "external" (not permanent component of the basic linac system) measurement equipment which is attached to the gantry 20. The "external" measurement is not required for the normal linac operation in the context of the radio therapy. The wire connected to the connector uses a similar path as other cables of the linac and is a permanent component of the linac. The energy supply is supported battery driven (as presented before) or by a power supply plug permanently mounted on the gantry 20. Since modern linacs are not equipped with data wires or a supply voltage for non permanent "external" devices, this is a feature of the invention.

The supply voltage and the data wires can be (but doesn't have to be) integrated in one single cable harness and are a permanent component of the linac. Alternatively, the accessory holder 44 is provided with data and power supply connectors 40 to the linac side and to the phantom side. (The phantom is connected to the accessory holder 44, and the accessory holder 44 is connected to the linac.). The date transfer techniques can be mixed.

Figure 16:
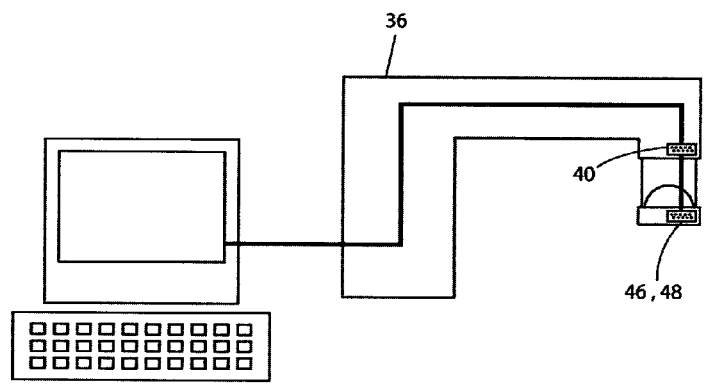
FIG. 16 is a schematic view showing data transfer and/or current supply for "external" measurement equipments which are not a permanent component of the basic linac.

Referring now to FIG. 16, preferably, data transfer and/or current supply for "external" measurement equipment which are not a permanent component of the basic linac 36 are provided via connectors 40, 46, 48 near the 2D array drawer 66 or on the gantry 20.

This makes the QC accessory 10 to a component of the linear accelerator and simplifies the handling to the user. This option is part of the patent application. (But this option is not essential for the QC accessory 10)

The Calculation Algorithm

Different from the "ArcCheck" phantom, the dose distribution is measured in the center of the phantom, where tumors are preferably situated and where the dose distribution is of particular interest.

Outside the measurement plane 106, calculation is needed. The dose calculation algorithm described below or the individual components of the algorithm or variants of them are considered a feature of the invention.

The dose calculation algorithm is based on the fact that the phantom has always the same position in the beam coordinate system 34, independent from the beam orientation in the room coordinate system. The absorption characteristic of the phantom is therefore independent of the irradiation technique and the geometrical beam parameters. It can be calculated in advance with a suitable full phantom, 360° rotationally symmetric (not only half of it=180° rotationally symmetric; as used for measurements).

The calculation of the absorption matrix is performed assuming the same conditions as when the verification plan is calculated and the verification is performed (same calculation algorithm—ideally but not necessarily, identical beam energy and the identical phantom shape). The isocenter of the beam is in the (virtual) axis (or point) of rotation of the phantom. The latter is consistent with the rotational axis of the gantry 20.

Calculation of the 3-Dimensional Absorption Matrix: (this Step has to be Performed Once.)

Referring now to FIGS. 17A and 17B, the dose distribution of a large irradiation field (hereinafter, based on techniques used in nuclear medicine, designated as a "flood field") is calculated, which covers the entire phantom.

A sketch for the flood field covering the entire phantom (right) and for a patient field (left). The gantry angle is 0°. Two points P and $P_{Det}$ lie on a line through the beam focus. $P_{Det}$ lies in the isocenter plane, which corresponds to the measurement plane 106 of the 2D array 14. P lies at any point of the calculation grid in the interior of the phantom. The isocenter line is perpendicular to the measurement plane 106 of the 2D array 14, which coincides with the isocenter plane. As seen from the focus, P may be placed ahead of or behind the isocenter plane.

The matrix term $A(P)=Dose(P)/Dose(P_{Det})$ describes the 3-dimensional absorption characteristics of the phantom. The three dimensional absorption matrix A(P) takes into account dose variations in the vicinity of density variations as adequate as the dose calculation algorithm, used to calculate the dose distribution of the flood field. The method assumes that lateral dose scatter equilibrium is present for each point in the phantom. That means that the scatter contributions to P are as large as the scatter contributions leaving P. A(P) is calculated for any point P of the calculation grid situated in the inner of the phantom. This calculation has to be performed only once, because the absorption matrix depends only on the material and methods used and the beam parameters. For any phantom and radiation energy combination, the absorption matrix must be determined separately. The application of a flood field and the method of applying an absorption matrix to calculate the dose distribution is also part of this Invention. Instead of an absorption matrix, the absorption can be described by the dose distribution of the flood field or mathematical functions or equivalent methods, or variants of it. These variations are also part of this Invention.

Steps to verify a patient's plan:

1. Taking into account systematic deviations: Irradiate the phantom with the flood field that has already been used to determine the absorption matrix, see FIG. 17B. Same geometry as used to calculate the absorption matrix: When systematic deviations would be not present, the same dose would be measured as calculated with the planning system in the isocenter plane. (It can be assumed that each planning system is able to calculate the dose distribution of such a simple field and phantom geometry reliably. This is valid especially for homogeneous phantoms and distant to density variations.) Among the systematic deviations are: Air pressure and temperature, different sensitivities of the detector elements of the 2D array 14, a small misplacement of the phantom body 30 relative to the incident beam 26, output fluctuations of the linear accelerator and deviations of the actual field homogeneity from the homogeneity assumed by the planning system . . . . It is assumed that the systematic deviations are the same when the patient plan fields are verified. (But it has to be minded that the correction is not valid for lateral displacements of the detector array itself!)

For each detector element i, the measured dose, $M_i$, is compared with the dose $C_i$, which has been calculated at the position of the detector element. A correction factor $S_i=C_i/M_i$ is determined for the $i^{th}$ detector. It takes into account all systematic deviations.

The 2-dimensional correction matrix S has to be determined only once at the beginning of a verification cycle, which may include multiple plan verifications. S will be applied to all field measurements of the verification cycle. The use of a flood field to correct for systematic deviations is part of the instant Invention.

2. Acquisition. Calculation of the "geometrical dose distribution" of a patient's field: Acquisition of a field (or field sequence, allocated to a gantry angle and collimator angle section), see FIG. 17A. The calculation is performed in the field coordinate system. This means that a 0° gantry and collimator angle is assumed for the primary calculation. An arbitrary point P in the inner of the phantom is considered. The point $P_{Det}$ lies on the connecting line of P and the beam focus. Additionally, $P_{Det}$ is situated in the detector plane. In general interpolation is needed to calculate $P_{Det}$. As presented in step 1, the dose $D(P_{Det})$ is corrected for systematic deviations. The "geometrical dose distribution", G(P), assigns the dose D($P_{Det}$) to the point P, see FIGS. 17A and 17B. In this way, all points located on the same line through the beam focus, become the same dose. This assignment is done on pure geometrical criteria.

3. Calculation of the "absorbed dose" for each point P, D(P): Multiplication of the geometrical dose of P, G(P), with the absorption factor A(P), assigned to P: D(P)=A(P)×G(P).

4. Subsequent corrections: Preliminary calculations have shown that the extrapolated dose fits very well to the calculated dose outside the isocenter (=measurement) plane. Due to the calculation method, the agreement is better when P is close to the Isocenter plane.

Additional corrections are suitable to increase the calculation accuracy Corrections which now can follow and lead to a further improvement of the dose calculation algorithm can be performed as shown below:
   a. The (local) dept dose depends on the field size and shape. A factor f(d) is applied to D(P). d is the distance of P to the isocenter plane, f(d)=1 for d=0; f(d)=c×d+1. c is a constant, depending on the field shape and size. This correction is a feature of the invention.
   b. Planes parallel to the measurement planes 106 are considered. The geometrical dose distribution does not account for scatter effects. These effects influence the relative dose distribution in a plane parallel to the measurement plane 106: For planes in front of the detector plane (seen from the beam focus), the dose distribution is contoured steeper, planes behind the measurement plane 106 show a more smeared dose distribution than the measurement plane 106. This can be taken into account by convolution and deconvolution methods. The (de)convolution strength depends on the distance and direction of the plane of interest to the measurement plane 106.

5. Coordinate System Transformation in the room coordinate system: The calculation has been performed until now in the beam coordinate system 34. This means that the gantry 20 (collimator 18, table 16 . . . when non coplanar techniques are applied) angles have been assumed to amount to 0°. Rotation of the dose distribution with respect to the effective beam incidence direction and gantry 20 orientation.

6. The total dose is determined by adding the dose contributions from all fields. When dynamic irradiation techniques are used: A "single field" contains the dose distribution applied for gantry and collimator angles of a "similar" amount, for example for a gantry angle between a and a+da, da=4°.

7. Calculation of the "measured patient dose in the room coordinate system (or CT image coordinate system)": The measured ($D_{m,ph}$) and calculated ($D_{c,ph}$) 3D dose matrixes in the phantom are known at that moment. This allows calculating the 3D dose ratio matrix in the phantom, $R_{ph}$. $R_{ph}=D_{m,ph}/D_{c,ph}$. The ratio matrix is multiplied point by point with the dose distribution in the original patients plan, $D_{c,pa}$, which has been calculated with the TPS (therapy planning system) and has to be verified. This results in the "measured patient dose", $D_{m,pa}$; $D_{m,pa}=D_{c,pa} \times R_{ph}$.

Alternative: Instead of the ratio matrix, the dose difference matrix can be used; $D_{d,ph}=D_{m,ph}-D_{c,ph}$. $D_{m,pa}=D_{c,pa}+D_{d,ph}$. Generally, a variety of operations (not only multiplication or difference) can be applied to transfer dose information from the phantom dose distribution to the patient dose distribution.

8. Evaluation options: Gamma index evaluation of $D_{m,pa}$ relative to $D_{c,pa}$, comparison of DVHs (dose volume histograms) of $D_{m,pa}$ and $D_{c,pa}$ for various contours of interest and representation of the difference curve. Graphical 3D representation of the difference or the gamma index value or DVHs (dose volume histograms). Alternatively, these evaluations can be performed in the dose distributions calculated and measured in the phantom. The evaluation software allows to switch between the phantom and the patient dose evaluations or to represent them simultaneously.

Note

Usually the phantom dose will be transferred to the patient geometry. Therefore the phantom geometry is in general not so relevant. It can be expected that all measurements are performed with hemispherical phantom bodies with different diameters.

At various calculation steps interpolations are required: The 2D array 14 measures only at discrete locations. The planning system calculates at discrete points, and the absorption matrix must be determined by interpolation, etc.

The consideration of systematic deviations (step 1 mentioned above) enables using a phantom body 30, which deviates from the assumed geometry. Example: The portion of the phantom body 30 near the detector is omitted. In the extreme case, the full phantom body 30 may be omitted. This procedures are useful to reduce the weight of the phantom body 30. The reduced scattering is then not taken into account. It can be compensated i.e. mathematically by smoothing, i.e, convolving the measured dose distribution. This option is also part of this Invention (see below).

Since systematic deviations are taken into account, detectors can also be used with an unknown measurement behavior. It is merely necessary that the signal is proportional to the applied dose and that the sensitivities of the detector elements is stable within a verification cycle.

Defect detectors can be replaced without any additional effort by another detector. The verification procedure is not influenced.

Instead of the absorption matrix, the dose distribution or other properties of the flood field could be used (for example a mathematical description of the absorption matrix with mathematical functions). This method is equivalent and is a feature of the invention.

The 3D dose distribution in the RSC phantom is shown simultaneously with the planning structures. This can be made for example 3-dimensional as BEV or 2-dimensional, for example, in the measurement plane 106.

Instead of flat detectors, curved detectors can also be used. This variation is treated by the calculation algorithm in a similar way as for flat panels. It is a feature of the invention.

Multiple (i.e.) parallel detector planes can also been used. Then the calculation algorithm applies additionally interpolations, based on multiple sampling points. This option is a feature of the invention.

The detectors can be integrated permanently in the phantom body 30, which is a feature of the invention.

Examples of RSC Phantom Body Shapes and their Variants

Adaption of the Phantom Size to the Patient Geometry

Phantom shapes with different sizes and shapes are available. The size and shape (for instance the diameter of the cylinder) can be adapted to the patient geometry. When the phantom size coincides with the size of the patient anatomy to irradiate, the expected dose level should be in the same magnitude. For example, a cylinder with a large diameter is suitable to verify treatments in the thorax and pelvis, a smaller cylinder in the neck or for smaller patients. This increases the value of the verification process. The option to offer different phantom sizes is a feature of the invention.

Variants and Virtualization

Original RSC phantoms show a rotational symmetry. It can be useful for different reasons to deviate from the rotationally symmetrical phantom shape. The main reason is to make the phantom lighter. The changed absorption behavior (in comparison to the rotationally symmetrical shape) is taken into account mathematically and/or, as shown in step 1 of the calculation process, by taking into account systematic deviations with the "flood field" correction technique. Additional modifications (for example taking into account the changed scatter behavior, for instance by convolution) are useful to get the measurement matrix from the initially symmetrical phantom shape. This two-step procedure, which includes the phantom shape modification and mathematical compensation of it, is in the following referred to as "virtualization". Modifications of the rotationally symmetrical phantom shape are called "variants". The virtualization process is a feature of the invention.

Continuous Variants from the Symmetric Shape (Examples), Virtualization

Figure 18:
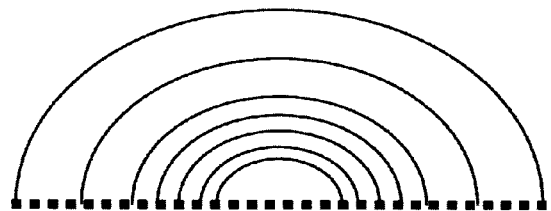
FIG. 18 is a schematic side view showing examples of continuous deviations from the symmetrical shape.

Referring now to FIG. 18, examples for continuous deviations from the symmetrical shape: Dependent on the patient's outline, different body shapes and sizes can be used.

Continuous variants from cylinder-shaped RSC phantoms: Different sizes, but same shape vs. change of the height to width relation for the full phantom or parts of it (for instance for the volume next to the 2D array 14).

Some Options and Properties

Similar to Matryoshka dolls, shells of different radii and densities can be stacked one on the other.

Due to the small weight of the individual components of the phantom, no transport trolley is needed to mount the phantom.

Figure 19:
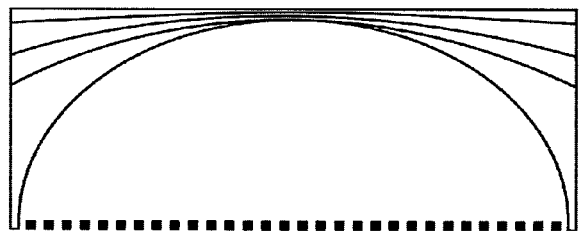
FIG. 19 is a front view of a continuous transformation of a cylindrical RSC phantom to a hemispherical RSC phantom.

RSC phantoms convert continuously from the cylinder-shaped form to a hemisphere (FIG. 19). Semispherical phantom bodies are suitable to verify non coplanar (isocentrical) irradiation techniques for arbitrary collimator angles. As they are RSC phantoms, they are a feature of the invention.

Referring now to FIG. 19, a continuous transformation of a cylindrical RSC phantom 12 to a hemispherical RSC phantom is shown.

The deviation from the rotational form is compensated by the measurement and calculationmethods 130, 140 presented herein, i.e. also known as the virtualization process.

Non Continuous Variants from the Symmetric Shape (Examples); Virtualization

Figure 20A:
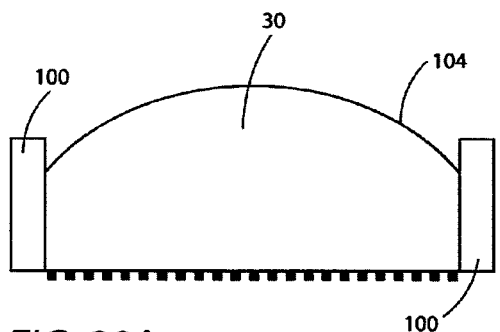
FIGS. 20A and 20B are schematics of a phantom body, showing possible omitted parts thereof.
Figure 20B:
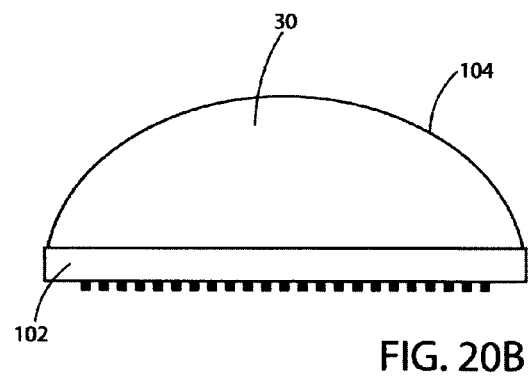

Parts of the phantom body 30 can be omitted that are not relevant to the measurement technique. (FIG. 12). The calculation algorithm presented above is able to take the "virtualization" of phantom parts into account ("virtualization" techniques are a feature of the invention). The measurement technique assumes that the position of the phantom relative to the focus is constant in the field coordinate system. This assumption can be violated by the gravity effect. A purpose of the visualization is to make the phantom body 30 lighter and to minimize the gravidity effect in this way:

Referring now to FIGS. 20A and 20B, omitting parts of the phantom body 30. To the left: The tangentially irradiated parts of the phantom define the dose contributions at the phantom surface 104, where the dose is in general not relevant. Right: the 2D array 14 adjacent to part of the phantom is omitted (highlighted in white).

Due to the properties of the calculation algorithm, continuous phantom body 30 variations, affecting only the height of the phantom body 30, should be preferred (for example a linear decrease of the local phantom height y which is a function of x and z: $y(x,z) \rightarrow a \times y(x,z); a<1$).

Shift of the Measurement Plane

Figure 21:
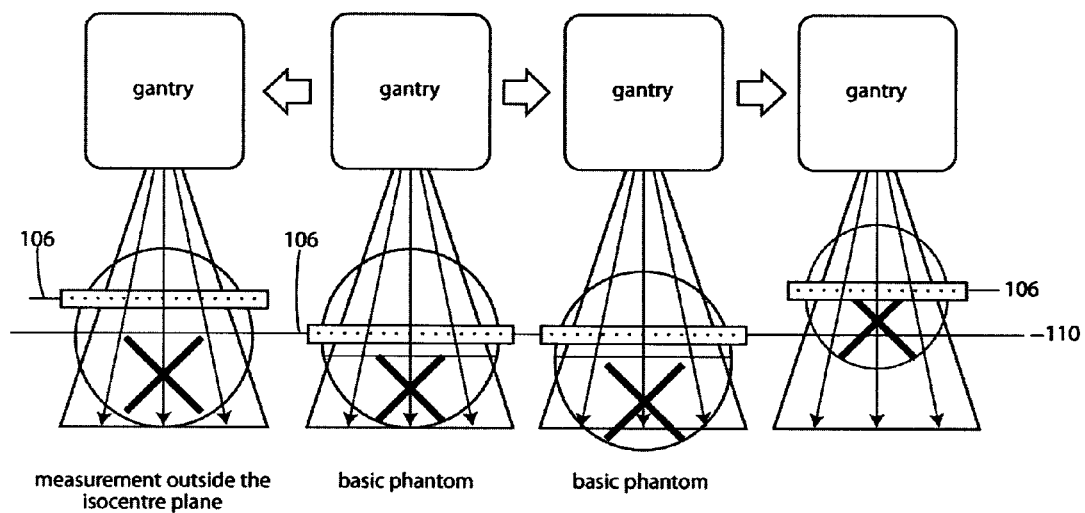
FIG. 21 shows how additional variants arise when the distance of the measurement plane relative to the focus is shifted.

Referring now to FIG. 21, additional variants arise when the distance of the measurement plane 106 relative to the focus 110 is shifted.

From left to right are shown: Measurement in another plane than the isocenter plane without a phantom shift/Original RSC method/Shift of the phantom body 30 position relative to the 2D array 14/Proportional reduction of the measurement setup and materials; diminution and shift to the focus Apart from phantoms with cylindrical phantom bodies, all other forms and variants are sought to be protected by this application. Particularly, the hemispherical phantom body 30 and its variants including virtualization need to be pointed out as enabling the verification of non coplanar irradiation techniques with varying collimator angles. In robot-assisted stereotactic radiation techniques, this option is of special interest.

Comments to the Virtualization Process

When the virtualization is performed in a high degree, the influence of the mathematical correction on the measurement-calculation accuracy is relevant: Since any correction introduces an additional error, it is crucial to find a compromise between a pure RSC technique and a virtualization based technique.

In the extreme case, the virtualization leads to a complete abandonment of the phantom body 30. The basic principle of the RSC calculation algorithm remains: As before, the 3D dose distribution is determined in a (virtual) RSC phantom, and the detector is oriented during the measurement series to the incoming central beam. This option is a feature of the invention.

Check of the Calculation Algorithm: Measurements in the "Inner" of the Phantom

Figure 22:
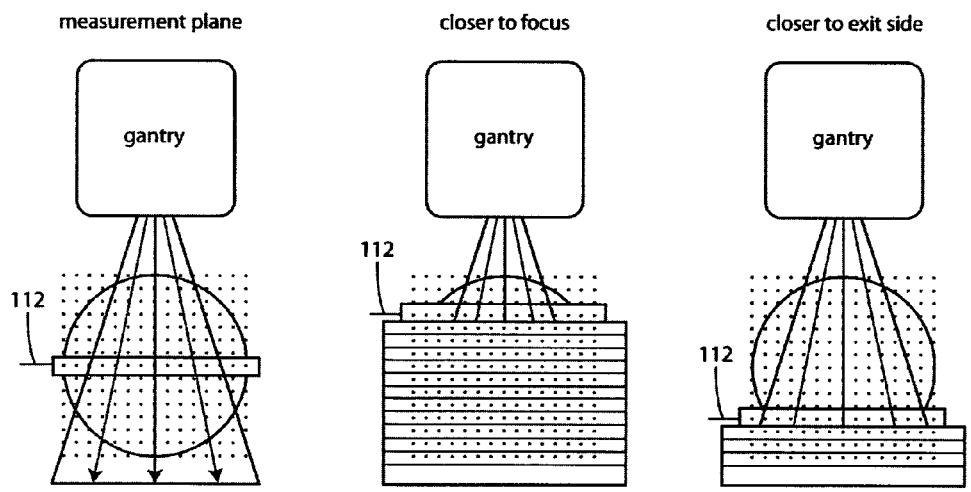
FIG. 22 is a schematic series of views illustrating a setup for measurement outside the diameter plane of the phantom.

Referring now to FIG. 22, setups for measurements outside the diameter plane 112 is shown. With a set of phantom plates 70, which complete to a RSC phantom body 30, measurements can be carried out in different planes in an "inner" plane through the phantom 12, for instance parallel to the measurement plane 106. This enables the measurement/calculation method and the correction algorithm of virtualization to be parameterized or tested:

Practical Implementation of RSC Phantoms: Some Details

With a hemispherical phantom, non coplanar irradiation techniques with varying collimator angles can be verified; for example in the head region. This has not been described in the literature to date, and is part of this Invention. RSC bodies can be constructed with materials of different density. The presented dose calculation algorithm is reliable even in these cases.

For the verification of TomoTherapy radiation treatments, the Phantom is appropriate only with great effort: The phantom cannot be fixed to the gantry 20. In this case a rotatable phantom placed on the treatment table 16 is suitable for dose verifications.

When cylindrical phantom bodies are used, composite measurements can be conducted. They are required when the Phantom is in the longitudinal axis too small to measure the full dose distribution. This can occur when a "half beam" technique is applied. (The field expands only in one direction, seen from the isocenter.) Then, the phantom (2D array 14 and phantom body 30) is moved along the gantry axis. Two measurements are performed, with dislocations in opposite directions. The measured dose distributions (or 2D measurements) are combined to an integral dose distribution (or 2D measurement). This procedure has not been described until now for 3D phantoms and is a feature of the invention application.

The Gantry Mount Device of the QC Accessory

Expansion of the field of application of the gantry holding device which is part of the QC accessory 10: The fixation device of the phantom (in the following called as "accessory") is mounted on the gantry 20 with the same technique as used for the block tray holder and the electron tubes. This technique differs from the techniques described elsewhere and so is a feature of the invention. The numeric code of the gantry fixing device (similar to other accessories) can be switched, so that both electron and photon fields can be applied. Alternatively the linac software accepts the accessory for photon as well as for electron beam irradiations. In this way, it is possible to check the radiation characteristics of both photonic and electronic fields, with the mounted 2D array 14 (for instance field homogeneity and symmetry; energy). Suitable absorbers 12 are available, which are plates that can be mounted on the 2D array 14 similar to the phantom bodies. An electron frame (forming the shape of electron fields) can be, similar to the phantom bodies, mounted to the gantry holder in the usual distance from the beam focus. By this means, a realistic field shape is formed, while the electronics of the 2D array 14 is protected from radiation. This option is a feature of the invention application. Additional inserts can be used to check the energy of the radiation fields, i.e. by performing absorption measurements. They are attached in a similar manner as the phantom body 30. Combined with the ability to perform MLC measurements, the gantry holder and the 2D array 14 become thus a universal instrument. The universality is a significant strength of the RSC phantom class.

Despite several advantages, the fixation technique and the specific properties of the accessory holder 44 described above are not essential for the QC accessory 10 concept.

Figure 23:
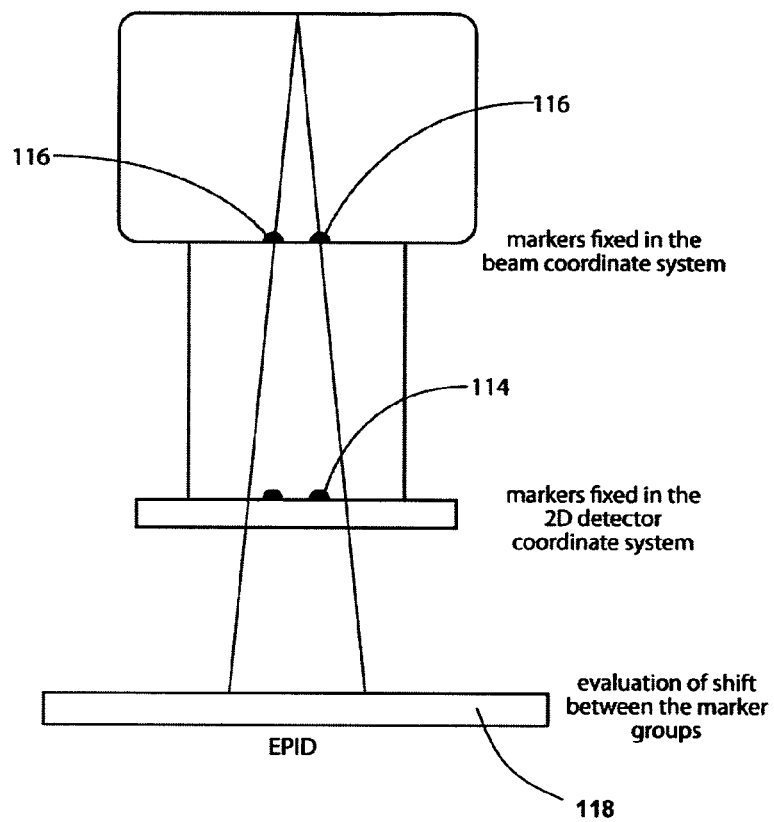
FIG. 23 is a schematic showing the measurement of gantry dependent shift of the 2d detector in the beam coordinate system.

Referring now to FIG. 23, the measurement of gantry dependent shift of the 2D detector 14 in the beam coordinate system 34 is shown. The gantry dependent relation between the 2D detector 14 and the beam coordinate system 34 can be measured with two opaque marker groups 114 and 116. One group 114 is attached to the 2d detector 14, the other group 116 to the beam exit window 54 on the gantry 20 (or another area, assumed to be fixed in the beam coordinate system 34). Images are acquired with the EPID (electronic portal imaging device) 118 for different gantry angles, and then evaluated.

The Machine QC Component of the QC Accessory

As described above, the 2D detector 14 is mounted on the gantry 20 similar to the block tray or electron tube accessory in a fixed and reproducible position. Machine checks can be performed therefore in the isocenter plane, independent on the gantry and collimator angle. These checks include:

Absolute MLC position measurements. The measurement is performed in the middle of the leaf end. Therefore a lateral movement of the 2D array 14 can be needed.

Absolute Field size (collimators or backup-collimator 18) measurement

Field symmetry and homogeneity. Lines, as an example, are engraved in the absorber 12 to check the light field position and size.

Energy and dose

Multiple absorbers 12 are available which fit to the specific measurement of interest. (When they can be exchanged automated, additional time can be saved.) Suitable measurement techniques are described in the literature. Depending on the degree of the gantry angle dependent gravidity effect, the displacement correction of the 2D array 14 in the field coordinate system can be conducted by applying shifts and rotations which depend on the gantry angle (and, if needed, the collimator rotation angle). They are obtained for different gantry (and collimator angles, if needed) once before the QC accessory 10 is used. When the collimator angle is constant for machine checks, for instance 0°, the corrections for translation and rotation are a function of the actual gantry angle.

For electron beams, a high Z frame (Z: atomic number) is mounted to the 2D array 14 similar to the phantom bodies or to absorbers 12. It defines the field shape of the electron beam and protects additionally the electronics of the 2D array 14 from irradiation damages.

When no longitudinal dislocation of the phantom is applied, the isocenter line coincides with the center of the 2D array 14 and with the center of the phantom. To check the entry point of the isocenter line in the phantom, a cross hair is attached on the surface of the phantom body 30, which is integrated into a label.

Additional symbols help to check the position of the isocenter line when the phantom is displaced. This is needed for instance when composite measurements are performed (see above).

Elements of the symbol refer also to the 3D dose measurement capacity of the phantom: The symbol consists of parts of the letter "D" (for "dimension" or "dose") and the figure "3". By the "hands" and "legs" of the symbol, vertices are shown, allowing checking the orientation of the field relative to the phantom.

A method 130 of using the quality control accessory for patient plan irradiation with the original variable gantry angles includes the steps of:

a. mounting the phantom in a functional manner, including establishing a communication link between the phantom and the acquisition software;

b. irradiating the phantom with a "flood field" and comparing the measured 2d dose distribution with the calculated dose distribution in order to correct for actual systematic errors;

c. for each gantry and collimator angle interval: applying the patient treatment plan to the phantom; acquisition of the corresponding 2d dose distribution and of the gantry 20 (and collimator angle, when varied);

d. for each gantry and collimator interval and each point within the housing of the phantom: multiplying point by point the "geometrical" dose distribution by the absorption matrix;

e. for each gantry and collimator angle interval: correcting of the 3d dose distribution (in the beam coordinate system 34) by taking into account the field shape dependent depth dose and scatter behavior outside the measurement plane, including both convolution and deconvolution, depending on the location of an arbitrary point P in the inside of the phantom relative to the measurement plane and the focus;

f. for each gantry and collimator angle interval: calculating the 3d dose distribution in the phantom (in the room coordinate system) by taking into account the gantry, collimator and table rotation g. addition of the 3d dose contributions of the angle intervals (in the room coordinate system);

h. transferring the calculated to measured dose deviation (difference or another deviation measure) from the phantom to the original patient plan represented in the CT slices in order to get the "measured" dose distribution in the patient; and i. comparing the calculated with the "measured" dose distribution in the patient, applying common dose comparison tools optionally referred to patient related structures as for instance dose volume histograms for patient related structures (critical organs, PTV, . . . ) and differences A method 140 of using the quality control accessory 10 for patient plan irradiation with a constant gantry angle, which is for instance 0° during the entire verification process includes the steps of:

a. mounting the phantom in a functional manner stationary in the room coordinate system with its symmetry axis parallel to the gantry axis of rotation, including establishing a communication link between the phantom and the acquisition software;

b. irradiating the phantom with a "flood field" and comparing the measured 2d dose distribution with the calculated dose distribution in order to correct for actual systematic errors;

c. for each gantry angle interval of the original patient plan: applying the patient treatment plan to the phantom without modifying the gantry angle; acquisition of the corresponding 2d dose distribution d. for each gantry angle interval and each point within the housing of the phantom: multiplying point by point the "geometrical" dose distribution by the absorption matrix;

e. for each gantry angle interval: correcting of the 3d dose distribution (in the beam coordinate system 34) by taking into account the field shape dependent depth dose and scatter behavior outside the measurement plane, including both convolution and deconvolution, depending on the location of an arbitrary point P in the inside of the phantom relative to the measurement plane and the focus;

f. for each gantry angle interval: calculating the 3d dose distribution in the room coordinate system) wherein information about the gantry angle in the patient plan, belonging to the measured 2d dose distribution, is either entered manually or obtained by other means (for instance from the DICOM file, which describes the integral irradiation technique), or by comparing the measured with (gantry dependent) expected 2d dose distribution;

g. addition of the 3d dose contributions of the angle intervals (in the room coordinate system);

h. transferring the calculated to measured dose deviation (difference or another deviation measure) from the phantom to the original patient plan represented in the CT slices in order to get the "measured" dose distribution in the patient; and i. comparing the calculated with the "measured" dose distribution in the patient, applying common dose comparison tools optionally referred to patient related structures as for instance dose volume histograms for patient related structures (e.g., critical organs, PTV, etc) and differences.

Figure 24:
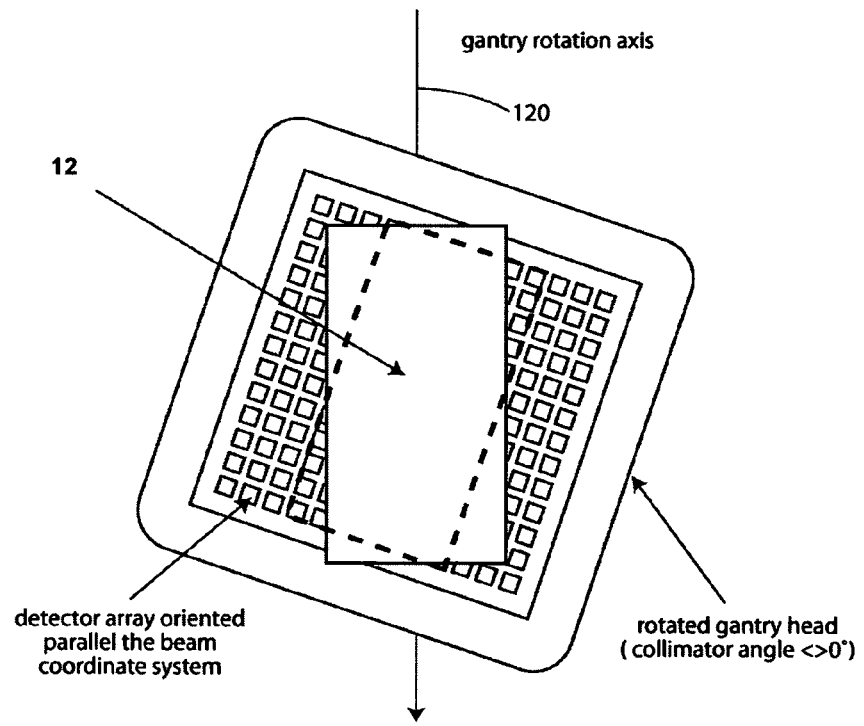
FIG. 24 is a schematic view of a phantom mounted such that the collimator angle is something other than 0 degrees.

Referring to FIG. 24, the above method 130 may also be applied when the collimator angle (the gantry head angle) is something other than 0°, in which case, the method includes the further steps of re-aligning the phantom body 30 with its rotational axis parallel to the gantry or linac rotational axis 120, the rotational orientation of the 2D detector 14 being arbitrary, but nonetheless oriented orthogonal to the beam. Note that here, the detector 14 is oriented parallel to the beam coordinate system 34.

The above methods 130 or 140 may of course be s parameterized and checked with a set of phantoms, such as shown in FIG. 22.

Referring now to FIG. 25, a measurement method 160 is provided to measure the 2d dose distribution "in the inner of the phantom" (assumed to be 360° rotational symmetric). The plates 170 complete to the rotationally symmetric phantom. The 2D detector 14 can be placed between these plates 170.

In addition, referring now to FIG. 26, a method 180 of composite measurement of a large 3D dose distribution, wherein multiple determinations of a 3D dose distribution are made applying one of the above methods 130, 140 at differing dislocations of the phantom body 30 within the beam coordinate system 34, for instance by moving the 2D detector 14 and the phantom body 30 parallel to the beam coordinate system 34, and the measurements combined to yield a single 3D dose distribution.

Summary: Characteristics of the QC Accessory

The QC accessory 10 consists of a 3D dose verification phantom and components (for instance, absorbers) needed for different machine parameter checks. The QC accessory 10 is fixed to the gantry 20 similar to other accessories.

The Phantom Component:

RSC phantoms are suitable to verify the 3D dose distribution of isocentric irradiation techniques with arbitrary collimator 18 (or table 16, i.e. for non-coplanar techniques) angles. RSC phantoms are rotationally symmetric with respect to an axis or a point (when suitable for non-coplanar irradiation techniques). The volume on the exit side of the beam relative to the 2D array 14 is not needed. Remember, that full and half phantom bodies are not distinguished here.

A 2D measurement device is placed in the diameter plane. Variations are described above. Apart from the rotational symmetry, the shape of the phantom and the density distribution inside the phantom are arbitrary. Also arbitrary are the 2D detector type and the material of the phantom body 30.

Parts of the 3D phantom component: The phantom body/bodies 30, the 2D array(s) 14, the accessory forming the gantry holding device, devices to identify the spatial orientation of the phantom (and the 2D array 14), integrated or attached to a component of the RSC phantom, A fixation of this components to the 2D array 14, a fixation of this components to the accessory.

The symmetry axis of the phantom coincides with the gantry rotation axis (non-coplanar techniques: the symmetry point coincides with the center point of rotation). The detector is aligned to the impinging beam. As previously stated, there are different methods to fulfill this requirement.

The 3D dose distribution outside the measurement plane is determined mathematically, i.e. by extrapolation along the beam path (details below).

To calculate the 3D dose contribution of all fields of the treatment plan (seen from the room coordinate system), the angles of incidence (gantry 20, collimator, table 16 . . . ) are taken into account. The total dose is determined by adding the dose contributions from all fields.

The phantom body portion located at the beam exit side of the 2D array 14 may be omitted if the array provides sufficient backscatter or mathematical methods compensate or correct the changed measurement signal. Variants are also members of the RSC phantom class. They consist of variants of the basic shape and density distribution, caused by, for example, continuous variations of the phantom body 30, accompanied by, for example, a continuous variation of a mathematical algorithm to compensate for the altered absorption and scatter conditions. The process of variation and numerical compensation is called as "virtualization".

The Machine QC Component:

The QC accessory 10 is usable for photon as for electron beams.

Parts of the machine QC component:
the 2D array 14 and the gantry holder
absorbers suitable for the measurement parameter of interest or to protect the electronics of the 2D array(s) 14
a rectangular frame (or multiple frames) used to define the outline of an electron beam.
fixation of this components to the 2D array 14 or to the accessory holder
data and power supply connections and connectors, for instance integrated in the linac (linear accelerator assembly)

Techniques to check different machine parameters are described in articles available to a person of ordinary skill in the art.

Components of this Patent Application

The QC accessory 10 consists of a gantry accessory including a 3D verification phantom, a suitable dose calculation algorithm and a machine QC component. The data and power supply connection can be integrated in the linac itself.

The 3D Verification Component:

The patent refers to RSC phantoms and its variants (except cylindrical shapes), including the virtualization process. The principle is explained in detail above.
Included in the patent are descendant variants brought about by . . . .
 the shape and density distribution of a coherent rotational Phantoms presented in its basic form to be changed.
 the detector is deformed. The influence on the measured dose distribution can be modeled with mathematical methods or corrected with suitable measurement methods.
 the detector moves away from the Isocenter plane, e.g., in the direction of the beam focus. The influence on the measured dose distribution is modeled with mathematical methods.
 multiple detectors (for instance in parallel together) are used.
The dose distribution outside of the 2D detector 14 is determined by the calculation algorithms described above, or derived algorithms of it.
For a detector, different phantom bodies are available.
Instead of a 2D-detector, multiple parallel or non parallel mounted detectors, or a 3D detector may be used. This allows additionally interpolation.
The calculation algorithm can be parameterized and checked with a set of phantom plates.
A measurement device suitable to define the gantry and collimator angles is integrated into the phantom or connected to it.

The Machine QC Component:

The universal mount allows measuring or calibrating different machine or beam parameters.
Checks of photon as well for electron beams are supported by the accessory holder
Multiple tools are available to perform these tests Details Can Be Found in the Text Above.

In an advantage, the QC accessory of the invention provides a class of phantoms whose use is suitable to all detectors_for reliable measurements, independent of the gantry angle and site of the incident beam.

In another advantage, the QC accessory 10 can be used for electron as well as for photon beam checks.

In another advantage, no additional wires for the data transfer or the power supply have to be installed before verification is performed: They are integrated in the linear accelerator. When measurements are performed, the 2D array is plugged to them.

Moreover, the system contemplates the use, sale and/or distribution of any goods, services or information having similar functionality described herein.

The specification and figures are to be considered in an illustrative manner, rather than a restrictive one and all modifications described herein are intended to be included within the scope of the Invention claimed, even if such is not specifically claimed at the filing of the application. Accordingly, the scope of the Invention should be determined by the claims appended hereto or later amended or added, and their legal equivalents rather than by merely the examples described above. For instance, steps recited in any method or process claims may be executed in any order and are not limited to the specific order presented in any claim. Further, the elements and/or components recited in any apparatus claims may be assembled or otherwise operationally configured in a variety of permutations to produce substantially the same result as the present Invention. Consequently, the Invention is not limited to the specific configuration recited in the claims.

Benefits, other advantages and solutions mentioned herein are not to be construed as critical, required or essential features or components of any or all the claims.

As used herein, the terms "comprises", "comprising", or any variation thereof, are intended to refer to a non-exclusive listing of elements, such that any process, method, article, composition or apparatus of the Invention that comprises a list of elements does not include only those elements recited, but may also include other elements described in this specification. The use of the term "consisting" or "consisting of" or "consisting essentially of" is not intended to limit the scope of the Invention to the enumerated elements named thereafter, unless otherwise indicated. Other combinations and/or modifications of the above-described elements, materials or structures used in the practice of the present Invention may be varied or otherwise adapted by the skilled artisan to other design without departing from the general principles of the Invention.

The patents and articles mentioned above are hereby incorporated by reference herein, unless otherwise noted, to the extent that the same are not inconsistent with this disclosure.

Other characteristics and modes of execution of the Invention are described in the appended claims.

Further, the Invention should be considered as comprising all possible combinations of every feature described in the instant specification, appended claims, and/or drawing figures which may be considered new, inventive and industrially applicable.

The copyrights in any appendix hereto are owned by the Applicant(s) or their assignee and, with respect to express Licensees of the rights defined in one or more claims herein, no implied license is granted herein to use the Invention as defined in the remaining claims. Further, vis-à-vis third parties, including the public, no express or implied license is granted to reproduce, prepare derivative works, distribute copies, display, or otherwise use this patent specification, inclusive of the appendix hereto and any computer program comprised therein, except as an appendix to a patent issuing hereon.

Multiple variations and modifications are possible in the embodiments of the Invention described here. Although certain illustrative embodiments of the Invention have been shown and described here, a wide range of modifications, changes, and substitutions is contemplated in the foregoing disclosure. While the above description contains many specifics, these should not be construed as limitations on the scope of the Invention, but rather as exemplifications of one or another preferred embodiment thereof. In some instances, some features of the present Invention may be employed without a corresponding use of the other features. Accordingly, it is appropriate that the foregoing description be construed broadly and understood as being given by way of illustration and example only, the spirit and scope of the Invention being limited only by the claims which ultimately issue in this application.

REFERENCE NUMBERS IN DRAWINGS

QC Accessory 10
Absorber (including phantom) 12
2D Array or detector 14
Curved Array 14'
Table 16
Collimator 18
Gantry 20
Orientation device 22
Isocenter point 24
Incident beam 26
Linac assembly 29
Phantom body 30
Gyroscope, Inclinometer, Gyrometer 32
Beam coordinate system 34
Linac head 36
Power supply connector 40
Power cable 42
QC Accessory holder/fixation plate 44
Power supply connector 46
Data connector on holder 48
Distance buffer/standoff 50
Fixation of phantom 52
Exit window 54
Braces 56
Fixation of 2D Array 60
Drawer for 2D Array 66
Phantom base plate 70
Fixation from plate to 2D array 72
Electron frame 80
Fixation from electron frame to 2D array 82
Marks 90
Omitted portions 100
Portion 102
Phantom surface 104
Measurement plane 106
Focus plane 110
Diameter plane 112
Marker group one 114
Marker group two 116
EPID 118
Linac rotation axis 120
Method of use 130
2$^{nd}$ method of use 140
Variant method 150
Another method 160
Plates 170
Method of composite measurement 80

What is claimed is:

1. A quality control accessory for use in linear accelerator quality control and in verification of an arbitrary isocentric radiation treatment plan wherein the accessory comprises:
a non-cylindrical rotationally symmetric absorber with a hemispherical shape and a density distribution; and, a single, substantially planar 2d detector array adapted to be fixed in a stationary spatial relationship with respect to the absorber, wherein the 2d detector array is adapted to be attached in one single fixed relative spatial relationship with respect to a beam focus of the linear accelerator, when a gantry is rotated, the gantry including a gantry rotation axis, so that a central axis of the beam is substantially orthogonal to the 2d detector array and a phantom axis of symmetry that is parallel to or aligned with a central axis of the gantry rotation axis.

2. The quality control accessory of claim 1, further including an orientation device adapted to maintain the 2d detector array and the absorber in a fixed relative spatial relationship with respect to the beam focus of the linear accelerator, when the gantry is rotated, so that the central axis of the beam is substantially orthogonal to the 2d detector and the phantom axis of symmetry that is parallel to or aligned with the central axis of the gantry rotation axis.

3. The quality control accessory of claim 1, wherein the 2d detector array is made up of one radiation detector connectable to a phantom body or to the absorber, as a function of a measurement method.

4. The quality control accessory of claim 1, further including a processor encoded with a calculation algorithm which takes into account specific geometrical properties of a phantom orientation relative to the beam.

5. The quality control accessory of claim 1, further comprising an orientation device, wherein the orientation device consists of an accessory holder, which fixes the 2d detector array to the gantry, in which a phantom body is replaced by absorbers suitable to a measurement parameter of interest, suitable when linear accelerator quality controls are performed.

6. The quality control accessory of claim 1, wherein a size density distribution and form of a phantom body is selected to match patient size and geometry.

7. The quality control accessory of claim 1, wherein a phantom body comprises a water equivalent material selected from one of a group of water equivalent materials consisting of RW3, VIRTUAL WATER, SOLID WATER; and PLASTIC WATER.

8. The quality control accessory of claim 1, wherein the absorber comprises: a container, the container being filled with water and being sealed.

9. The quality control accessory of claim 1, further comprising an orientation device, wherein the orientation device is a QC accessory holder optionally fixed to the gantry.

10. The quality control accessory of claim 6, further comprising a QC accessory holder, wherein the QC accessory holder supports the application of photon as well as electron beams in a context of quality controls of different beam parameters.

11. The quality control accessory of claim 6, further comprising a QC accessory holder, wherein the QC accessory holder comprises one or more absorbers suitable for linear accelerator checks, the absorbers being fixed to the QC accessory holder or the 2d detector array in a manner similar to phantom bodies.

12. The quality control accessory of claim 6, further comprising a QC accessory holder, wherein the QC accessory holder further includes one or more frames to define field edges of electron fields, the frames being mounted to the 2d detector array or the QC accessory holder.

13. The quality control accessory of claim 1, wherein the 2d detector array or a plurality of 2d detector arrays are permanently integrated into a phantom body.

14. The quality control accessory of claim 1, further comprising an orientation device, wherein the orientation device comprises a mounting system, the mounting system structurally and fixedly mounting the 2d detector array and a phantom body in a region of a treatment table in order to rotate the 2d detector array and the phantom body with respect to the gantry and therefore with respect to a beam focus.

15. The quality control accessory of claim 1, further comprising an orientation device, wherein the orientation device further comprises:
   a guide for guiding a phantom along a path so as to maintain a fixed spatial orientation of the 2d detector array, and in which the 2d detector array is continuously held orthogonal to the gantry and therefore to an incident beam, and
   a motor for driving the phantom along a path.

16. The quality control accessory of claim 1, wherein the quality control accessory includes or is connectable to a device, the device selected from the group consisting of an inclinometer, a gyroscope and a gyrometer.

17. The quality control accessory of claim 1, further comprising a phantom, wherein the phantom includes or is connectable to a device to measure an angle of an isocentric table rotation, the isocentric table being useful in applying non coplanar irradiation techniques.

18. The quality control accessory of claim 1, wherein the quality control accessory further comprises a data transmission device, the data transmission device being adapted to transmit a geometrical orientation and/or dose information of the 2D detector array electromagnetically or by ultrasound.

19. The quality control accessory of claim 1, wherein the 2d detector array is powered by a battery mounted to a phantom, the phantom selected from the group consisting of a 2d detector, a phantom body, a structure of an orientation means, and a gantry.

20. The quality control accessory of claim 1, wherein the gantry comprises one or more provides plugs for a data connection and an energy supply of the 2d detector array and, optionally, a device for measuring a gantry and collimator angle.

21. The quality control accessory of claim 1, wherein a shape of a phantom body is not semi-rotationally symmetric and at a deviation, the deviation being of a magnitude that does not prevent a measured dose distribution of a rotationally symmetric phantom from being determined from a measured dose distribution in a 2d detector plane.

22. The quality control accessory of claim 18, wherein influence of deviation on a signal of the 2d detector array is determined by a mathematical algorithm or by a measurement in order to reconstruct an expected 2d detector signal when using the rotationally symmetric phantom.

23. The quality control accessory of claim 1, further comprising a fully symmetrical phantom body having adsorption properties, wherein the absorption properties of the fully symmetrical phantom body are determined by calculating a 3d dose distribution of a large radiation field which covers the whole phantom.

* * * * *